US010695235B2

(12) United States Patent
Thomas et al.

(10) Patent No.: US 10,695,235 B2
(45) Date of Patent: Jun. 30, 2020

(54) PRINTED 3D-ELASTIC LAMINATES

(71) Applicant: Kimberly-Clark Worldwide, Inc., Neenah, WI (US)

(72) Inventors: Oomman P. Thomas, Alpharetta, GA (US); Simon K. Poruthoor, Alpharetta, GA (US); Charles Morell, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 698 days.

(21) Appl. No.: 14/091,432

(22) Filed: Nov. 27, 2013

(65) Prior Publication Data
US 2015/0147539 A1    May 28, 2015

(51) Int. Cl.
*A61F 13/49* (2006.01)
*B32B 27/12* (2006.01)
(Continued)

(52) U.S. Cl.
CPC .......... *A61F 13/4902* (2013.01); *A61F 13/84* (2013.01); *B32B 5/022* (2013.01);
(Continued)

(58) Field of Classification Search
CPC ................. A61F 13/4902; A61F 13/84; A61F 2013/49031; A61F 2013/8497;
(Continued)

(56) References Cited

U.S. PATENT DOCUMENTS 3,338,992 A    8/1967 Kinney
3,341,394 A    9/1967 Kinney
(Continued)

FOREIGN PATENT DOCUMENTS

EP    0748894 A2    12/1996
EP    0748894 A3    12/1996
(Continued)

OTHER PUBLICATIONS

Elastomer Chemical Compound, Encyclopedia Britannica, https://www.britannica.com/science/elastomer, retrieved May 9, 2019.*
(Continued)

*Primary Examiner* — Jennifer A Gillett
(74) *Attorney, Agent, or Firm* — Dority & Manning, P.A.

(57) ABSTRACT

An aesthetically pleasing elastic film with three-dimensional characteristics is provided. In one embodiment, a two-dimensional ink structure is printed onto an elastic film, which is then activated, for example, by heat, which transforms the two-dimensional ink structure into a three-dimensional ink structure on one or more outer surfaces of the film. The location and amount of ink applied can be selectively controlled so that the film has the desired hand feel without sacrificing the elastic properties of the film. Further the printing and activating of the ink can be controlled to increase the tear resistance of the film or to conversely allow the film to tear or rip at desired locations on demand. In another embodiment, the elastic film can be laminated to a facing to form a laminate, where the outer surface of the film that is not in contact with the facing contains the three-dimensional ink structures.

12 Claims, 8 Drawing Sheets

(51) Int. Cl.
- *A61F 13/84* (2006.01)
- *B32B 27/32* (2006.01)
- *B32B 5/08* (2006.01)
- *B32B 27/30* (2006.01)
- *B32B 5/02* (2006.01)
- *C08J 5/18* (2006.01)

(52) U.S. Cl.
CPC ............... *B32B 5/08* (2013.01); *B32B 27/12* (2013.01); *B32B 27/302* (2013.01); *B32B 27/32* (2013.01); *C08J 5/18* (2013.01); *A61F 2013/49031* (2013.01); *A61F 2013/8497* (2013.01); *B32B 2262/0253* (2013.01); *B32B 2262/0261* (2013.01); *B32B 2307/4026* (2013.01); *B32B 2307/51* (2013.01); *B32B 2307/518* (2013.01); *B32B 2307/54* (2013.01); *B32B 2307/726* (2013.01); *B32B 2437/00* (2013.01); *B32B 2555/02* (2013.01); *C08J 2323/04* (2013.01); *C08J 2323/10* (2013.01); *Y10T 156/1007* (2015.01); *Y10T 428/2481* (2015.01); *Y10T 428/24802* (2015.01)

(58) Field of Classification Search
CPC ... B32B 5/022; B32B 5/08; B32B 2307/4023; B32B 2307/51; B32B 2555/00; B32B 2555/025; Y10T 428/4802; Y10T 428/2481; C08J 2323/04; C08J 2323/10; C08J 5/18; D06N 2209/0815
USPC ...... 442/394, 328; 428/103, 195.1, 196, 156
See application file for complete search history.

(56) References Cited

U.S. PATENT DOCUMENTS

| | | | |
|---|---|---|---|
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,963,656 A | 6/1976 | Meisert et al. | |
| 4,323,534 A | 4/1982 | DesMarais | |
| 4,340,563 A | 7/1982 | Appel et al. | |
| 4,663,220 A | 5/1987 | Wisneski et al. | |
| 4,789,592 A | 12/1988 | Taniguchi et al. | |
| 4,795,668 A | 1/1989 | Krueger et al. | |
| 4,834,738 A | 5/1989 | Kielpikowski et al. | |
| 4,937,299 A | 6/1990 | Ewen et al. | |
| 4,965,122 A | 10/1990 | Morman | |
| 4,981,747 A | 1/1991 | Morman | |
| 5,069,970 A | 12/1991 | Largman et al. | |
| 5,093,422 A | 3/1992 | Himes | |
| 5,108,820 A | 4/1992 | Kaneko et al. | |
| 5,162,074 A | 11/1992 | Hills | |
| 5,218,071 A | 6/1993 | Tsutsui et al. | |
| 5,226,992 A | 7/1993 | Morman | |
| 5,272,236 A | 12/1993 | Lai et al. | |
| 5,277,976 A | 1/1994 | Hogle et al. | |
| 5,278,272 A | 1/1994 | Lai et al. | |
| 5,304,599 A | 4/1994 | Himes | |
| 5,322,728 A | 6/1994 | Davey et al. | |
| 5,332,613 A | 6/1994 | Taylor et al. | |
| 5,336,545 A | 8/1994 | Morman | |
| 5,336,552 A | 8/1994 | Strack et al. | |
| 5,382,400 A | 1/1995 | Pike et al. | |
| 5,466,410 A | 11/1995 | Hills | |
| 5,472,775 A | 12/1995 | Obijeski et al. | |
| 5,507,368 A | 4/1996 | Barefoot | |
| 5,539,056 A | 7/1996 | Yang et al. | |
| 5,571,619 A | 11/1996 | McAlpin et al. | |
| 5,596,052 A | 1/1997 | Resconi et al. | |
| 5,605,961 A | 2/1997 | Lee et al. | |
| 5,873,641 A | 2/1999 | Spinelli | |
| 5,932,497 A | 8/1999 | Morman et al. | |
| 5,997,981 A | 12/1999 | McCormack et al. | |
| 6,008,276 A | 12/1999 | Kalbe et al. | |
| 6,015,764 A | 1/2000 | McCormack et al. | |
| 6,090,325 A | 7/2000 | Wheat et al. | |
| 6,111,163 A | 8/2000 | McCormack et al. | |
| 6,200,669 B1 | 3/2001 | Marmon et al. | |
| 6,231,719 B1 | 5/2001 | Garvey et al. | |
| 6,417,313 B2 | 7/2002 | Spyrou | |
| 6,432,527 B1* | 8/2002 | Perez | B29D 7/01 428/343 |
| 6,440,533 B1* | 8/2002 | Ray | B32B 27/32 264/173.14 |
| 6,461,457 B1 | 10/2002 | Taylor et al. | |
| 6,500,563 B1 | 12/2002 | Datta et al. | |
| 6,541,098 B2* | 4/2003 | Venkatasanthanam | B29C 47/0021 156/244.15 |
| 6,682,803 B2 | 1/2004 | McCormack | |
| 6,737,114 B2 | 5/2004 | Dawson, Jr. et al. | |
| 6,992,159 B2 | 1/2006 | Datta et al. | |
| 7,045,650 B2 | 5/2006 | Lawrey et al. | |
| 7,303,642 B2 | 12/2007 | Topolkaraev | |
| 7,320,948 B2 | 1/2008 | Morman et al. | |
| 7,393,811 B2 | 7/2008 | Chervin | |
| 7,806,880 B2 | 10/2010 | Roe et al. | |
| 7,816,285 B2 | 10/2010 | MacDonald et al. | |
| 7,887,522 B2 | 2/2011 | Roe et al. | |
| 7,943,813 B2 | 5/2011 | Petryk et al. | |
| 7,972,681 B2 | 7/2011 | Roys et al. | |
| 8,287,677 B2 | 10/2012 | Lake et al. | |
| 8,303,561 B2 | 11/2012 | Eriksson | |
| 8,445,110 B2 | 5/2013 | Shi et al. | |
| 8,603,281 B2 | 12/2013 | Welch et al. | |
| 8,900,690 B2 | 12/2014 | Baldauf et al. | |
| 2002/0045879 A1* | 4/2002 | Karami | A61F 13/49011 604/391 |
| 2004/0127872 A1* | 7/2004 | Petryk | A61F 13/51305 604/382 |
| 2004/0166248 A1* | 8/2004 | Hu | B01J 2/16 427/553 |
| 2005/0124952 A1 | 6/2005 | Zehner et al. | |
| 2005/0191470 A1* | 9/2005 | Roys | B41M 1/12 428/195.1 |
| 2006/0057291 A1 | 3/2006 | Duris et al. | |
| 2006/0100312 A1 | 5/2006 | Hall et al. | |
| 2006/0135728 A1 | 6/2006 | Peerlings et al. | |
| 2006/0137568 A1* | 6/2006 | MacDonald | A61F 13/5514 106/31.13 |
| 2006/0151914 A1 | 7/2006 | Gerndt et al. | |
| 2007/0003764 A1 | 1/2007 | Muslet et al. | |
| 2007/0049719 A1 | 3/2007 | Brauer et al. | |
| 2007/0141352 A1 | 6/2007 | Calhoun et al. | |
| 2007/0148410 A1 | 6/2007 | Wimer et al. | |
| 2007/0218791 A1 | 9/2007 | Lee et al. | |
| 2008/0027406 A1* | 1/2008 | Shirai | A61F 13/49009 604/385.24 |
| 2008/0063806 A1* | 3/2008 | Janssen | B05D 3/029 427/508 |
| 2008/0145532 A1* | 6/2008 | McDonald | B29C 44/1271 427/244 |
| 2009/0047477 A1 | 2/2009 | Roys et al. | |
| 2009/0087648 A1* | 4/2009 | Lee | B32B 27/08 428/336 |
| 2009/0177176 A1* | 7/2009 | Saito | A61F 13/49017 604/385.29 |
| 2009/0258210 A1* | 10/2009 | Iyad | A61F 13/15593 428/220 |
| 2010/0028638 A1 | 2/2010 | Reichardt et al. | |
| 2010/0051220 A1* | 3/2010 | Hong | B01J 13/14 162/138 |
| 2012/0094091 A1 | 4/2012 | van Mil et al. | |
| 2012/0157949 A1 | 6/2012 | Knight et al. | |

(56) References Cited

U.S. PATENT DOCUMENTS

2012/0157952 A1   6/2012   Poruthoor et al.
2012/0232511 A1   9/2012   Velazquez et al.

FOREIGN PATENT DOCUMENTS

| TW | M441565 U1 | 11/2012 | |
|---|---|---|---|
| WO | WO 97/00656 A1 | 1/1997 | |
| WO | WO 2011/045686 A1 | 4/2011 | |
| WO | WO 2013/001381 A2 | 1/2013 | |
| WO | WO 2013/001418 A2 | 1/2013 | |
| WO | WO 2013051971 A1 | 4/2013 | |
| WO | WO-2013077789 A1 * | 5/2013 | ............... C09J 7/38 |

OTHER PUBLICATIONS

Abstract of Japanese Patent—JP2001279571, Oct. 10, 2001, 2 pages.
International Search Report and Written Opinion for PCT/IB2014/064969 dated Feb. 6, 2015, 13 pages.

* cited by examiner

PRINTED 3D-ELASTIC LAMINATES

BACKGROUND OF THE INVENTION

Elastic films have been utilized in a variety of articles as a means of providing a stretch to the articles. As an example, elastic films have been utilized in absorbent articles such as diapers and incontinence garments, protective apparel and other articles. Elastic films are typically employed in such articles to improve their ability to better fit the contours of the body. As such, it is desirable that the amount of stretch be controlled so that the films stretch enough to be comfortable to the wearer while at the same time not stretching too much, which can negatively impact the fit of the articles in which the films are employed.

However, in addition to providing the desired stretch function, since these articles are often worn or handled, it is also desirable that the articles have a pleasing touch, feel, or "hand." As such, nonwoven facings can be attached to one or both sides of elastic films so that the film has a look, drape, and feel similar to that of cloth or other apparel fabrics. However, such nonwoven facings covering the entire film surface are expensive and time consuming to produce. Further, they may require additional adhesive and lamination steps, which can further increase costs. As such, providing a cost-efficient elastic film capable of exhibiting controlled stretch properties while likewise having good drape and hand has proven to be challenging. Thus, there exists a need for economically produced films having improved visual and/or tactile properties which also exhibit and retain excellent mechanical properties.

Further, elastic films often block or become sticky and fuse/adhere to each other when wound into rolls for storage, which can make it challenging to handle such films when converting the films into various products by additional processing. Additionally, it is often challenging but desirable to control the location at which elastic films stretch and the location at which the elastic films intentionally tear or intentionally rip upon overstretching. As such, a need currently exists for an aesthetically pleasing elastic film that blocks less when wound into a roll yet maintains desirable stretch properties. It is further desirable to engineer a film that rips or stretches at intended locations and that has improved overall tear resistance.

SUMMARY OF THE INVENTION

In accordance with one embodiment of the present invention, an elastic film having a machine direction and a cross-machine direction is disclosed. The film includes a first outer-facing surface, a second outer-facing surface, and three-dimensional ink structures, wherein each of the three-dimensional ink structures is present on the first outer-facing surface in a pattern extending in a predominant direction, wherein a continuous gap exists between adjacent three-dimensional ink structures, and further wherein the film is stretchable along the continuous gap in a direction that is generally perpendicular to the predominant direction in which the three-dimensional ink structures extend.

In one embodiment, the pattern comprises an individual line, groups of lines, groups of S-shapes, groups of discrete dots, groups of repeating geometric shapes, or combinations thereof.

In an additional embodiment, the three-dimensional ink structures have a width in either the machine direction or cross-machine direction ranging from about 0.25 mm to about 25 mm, wherein the width is perpendicular to the predominant direction of the pattern. In still another embodiment, the continuous gap spans a distance in either the machine direction or the cross-machine direction ranging from about 0.5 mm to about 20 mm, wherein the distance is perpendicular to the predominant direction of the pattern.

In another embodiment, the predominant direction of the pattern runs along the machine direction of the film. Further, in such an embodiment, the continuous gap also runs along the machine direction of the film. In addition, in such an embodiment, the three-dimensional ink structures can have a width in the cross-machine direction ranging from about 0.25 mm to about 25 mm. Moreover, in such an embodiment, the continuous gap can span a distance in the cross-machine direction ranging from about 0.5 mm to about 20 mm.

In still another embodiment, the predominant direction of the pattern runs along the cross-machine direction of the film. In such an embodiment, the continuous gap runs along the cross-machine direction of the film. In addition, in such an embodiment, the three-dimensional ink structures can have a width in the machine direction ranging from about 0.25 mm to about 25 mm. Moreover, in such an embodiment, the continuous gap can span a distance in the machine direction ranging from about 0.5 mm to about 20 mm. In yet another embodiment, the three-dimensional ink structures can have a thickness in a z-direction ranging from about 0.01 mm to about 5 mm.

In another embodiment of the present invention, the film described in the present disclosure can be a component of an absorbent personal care article.

In still another embodiment, the film of claim 1 can be part of a laminate that also includes a nonwoven facing layer, wherein the nonwoven facing layer is attached to the second, outer-facing surface of the film.

In still another embodiment, the film can include a core layer positioned between opposing first and second skin layers. The core layer can include a propylene-based elastomer, a polyethylene-based elastomer, a styrenic block copolymer, or a combination thereof, while the first and second skin layers can include a linear low density polyethylene.

In yet another embodiment, the predominant direction of the pattern can be at an angle that ranges from about 15° to about 90° relative to the cross-machine direction of the film.

In accordance with another embodiment of the present invention, a method of producing an elastic film having a machine direction and a cross-machine direction is disclosed. The method includes extruding an elastic film, printing a two-dimensional ink on a first outer-facing surface of the film in a pattern, and activating the two-dimensional ink to form three-dimensional ink structures on the outer-facing surface of the film. Further, the three-dimensional ink structures extend in a predominant direction, a continuous gap exists between adjacent three-dimensional ink structures, and the film is stretchable along the gap in a direction that is generally perpendicular to the predominant direction in which the three-dimensional ink structure extends.

In an additional embodiment, the film includes a core layer positioned between a first skin layer and a second skin layer, wherein the ink is printed on an outer-facing surface of the second skin layer.

In yet another embodiment, the film can be treated with a corona treatment or a plasma treatment prior to printing the two-dimensional ink on the outer-facing surface of the film.

In still another embodiment, two-dimensional ink is activated by heating the film to a temperature ranging from about 50° C. to about 200° C.

In yet another embodiment, the predominant direction of the pattern can run along the machine direction of the film, while in another embodiment, the predominant direction of the pattern can run along the cross-machine direction of the film.

In one more embodiment, a nonwoven facing can be laminated to a second, outer-facing surface of the film to form a laminate. Further, the laminate can be rendered elastically active by decoupling the nonwoven facing or by passing the laminate over a grooved roll. For instance, the nonwoven facing can be grooved in the machine direction to provide the laminate with stretch in the cross-machine direction. On the other hand, the nonwoven facing can be grooved in the cross-machine direction to provide the laminate with stretch in the machine direction. Further, the grooving in the nonwoven facing can be formed in a location that corresponds with the continuous gap in a z (depth) direction. In addition, in some embodiments, the nonwoven facing can be grooved in the machine direction and the cross-machine direction to provide the laminate with biaxial stretch. In such embodiments, the pattern of the ink can include discrete dots.

In accordance with still another embodiment of the present invention, a film having a machine direction and a cross-machine direction is disclosed. The film includes a first outer-facing surface, a second outer-facing surface, and three-dimensional ink structures. Each of the three-dimensional ink structures is present on the first outer-facing surface in a pattern extending in a predominant direction, wherein a continuous gap exists between adjacent three-dimensional ink structures. In one particular embodiment, the film can be elastic, while in another particular embodiment, the film can be inelastic.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
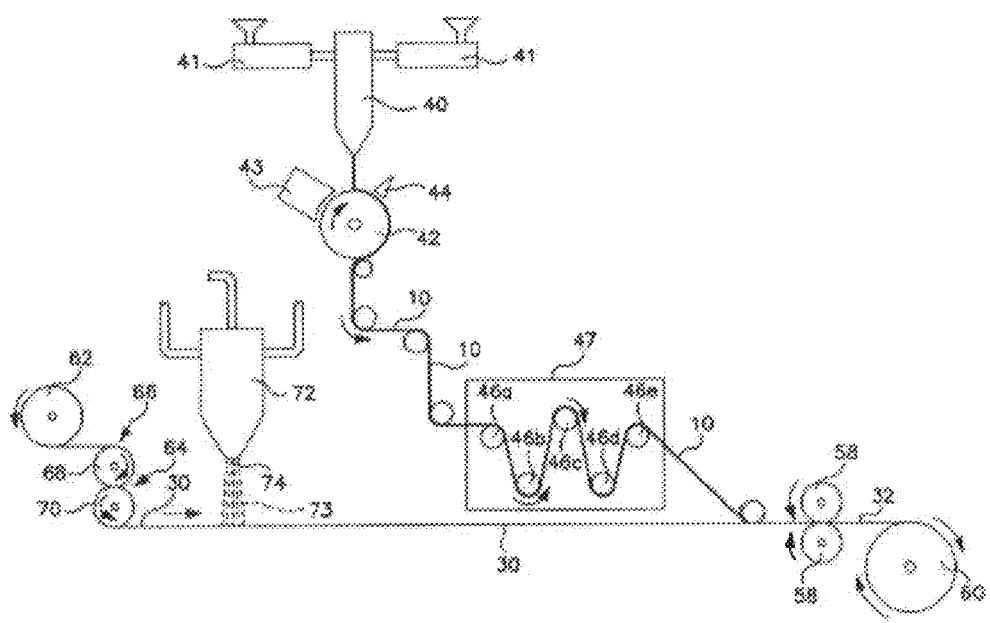
FIG. 1 schematically illustrates a method for forming an elastic film and optional laminate according to one embodiment of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the terms "machine direction" or "MD" generally refers to the direction in which a material is produced. The term "cross-machine direction" or "CD" refers to the direction perpendicular to the machine direction. Dimensions measured in the cross-machine direction (CD) are referred to as "width" dimensions, while dimensions measured in the machine direction (MD) are referred to as "length" dimensions.

As used herein, the terms "elastomeric" and "elastic" generally refer to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of at least 1.25 inches. Desirably, the material contracts or recovers at least 50%, and even more desirably, at least 80% of the stretched length.

As used herein the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, bonded carded webs, airlaid webs, coform webs, hydraulically entangled webs, and so forth.

As used herein, the term "meltblown" web or facing generally refers to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes.

As used herein, the term "spunbond" web or facing generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 3,338,992 to Kinney, U.S. Pat. No. 3,341,394 to Kinney, U.S. Pat. No. 3,502,538 to Levy, U.S. Pat. No. 3,502,763 to Hartman, U.S. Pat. No. 3,542,615 to Dobo et al., U.S. Pat. No. 3,692,618 to Dorschner, et al., U.S. Pat. No. 3,802,817 to Matsuki, et al., U.S. Pat. No. 4,340,563 to Appel, et al., and U.S. Pat. No. 5,382,400 to Pike, et al., which are incorporated herein in their entirety by reference thereto for all purposes. Spunbond fibers are generally not tacky when they are deposited onto a collecting surface and can have a diameter of from about 10 to about 20 micrometers.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features will be represented by like numbers between the figures. Thus, it is intended that the present invention cover such modifications and variations.

Generally speaking, the present invention is directed to an elastic film printed with one or more two-dimensional ink structures that can be activated into three-dimensional structures so as to impart the desired aesthetic, feel (surface topography) stretch, intentional (on demand) rip/tear, and anti-blocking properties to the film. Through selective control over certain parameters of the materials employed in the film, such as the three-dimensional ink structures and film components, the present inventors have discovered that an elastic film and laminate with controlled stretch properties can be formed. Further, laminates formed in accordance with the present invention do not require stretching and gathering to activate the elastic film and/or additional facing layers.

In one embodiment, the elastic film may possess a multilayered construction that includes an elastic layer (core layer) positioned adjacent to or between one or more thermoplastic layers (skin layers). The film has a soft hand or feel due to the presence of an activated two-dimensional ink that can be rendered three-dimensional after it is printed on at least one of the surfaces of the film. Further, the film is aesthetically pleasing yet maintains its stretch properties.

Further, the texture imparted by the three-dimensional ink that is present on at least one outer surface of the film or laminate prevents blocking of the film or laminate when stored on a roll or the need for outer facings on both sides of the film.

Specifically, an ink can be printed onto an elastic film which is then activated, for example, by heat, ultraviolet exposure, etc., which "puffs" or transforms a two-dimensional ink structure into a three-dimensional structure on one or more outer surfaces of the film. Further, the printing and ink activation can be done in such a way as to increase the tear resistance of the film or laminate to conversely weaken the film or laminate so that it intentionally rips or tears at desired places on demand.

Further, although the present invention as discussed below contemplates an elastic film on which three-dimensional ink structures are disposed to create a cloth-like feel similar to that of a nonwoven facing, it is also to be understood that, in some embodiments, it may be desirable for the film to be an inelastic film on which three-dimensional ink structures are disposed to create a cloth-like feel. In any event, the three-dimensional ink structures can have a similar feel to a nonwoven facing and can be used to replace the nonwoven facing in various applications, such as in absorbent article applications.

In this regard, various embodiments of the present invention will now be described in more detail.

I. Elastic Film

The elastic film of the present invention is formed from one or more layers of polymers that are melt-processable, i.e., thermoplastic. For instance, in one particular embodiment, the elastic film can be a monolayer film. In other embodiments, the elastic film can include two, three, four, five, or six layers. For example, a three-layer film that comprises a core layer sandwiched between two skin layers. However, it is to be understood that any number of layers can be present, where the one or more layers are formed from the same or different materials.

a. Core Layer

Any of a variety of thermoplastic elastomeric or plastomeric polymers may generally be employed in the present invention, such as elastomeric polyesters, elastomeric polyurethanes, elastomeric polyamides, elastomeric copolymers, elastomeric polyolefins, and so forth. In one embodiment, for instance, a substantially amorphous block copolymer may be employed that contains blocks of a monoalkenyl arene and a saturated conjugated diene. Such block copolymers are particularly useful in the present invention due to their high degree of elasticity.

The monoalkenyl arene block(s) may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene block(s) may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth. The amount of monoalkenyl arene (e.g., polystyrene) blocks may vary, but typically constitute from about 8 wt. % to about 55 wt. %, in some embodiments from about 10 wt. % to about 35 wt. %, and in some embodiments from about 15 wt. % to about 25 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable thermoplastic elastomeric copolymers are available from Kraton Polymers LLC of Houston, Tex. under the trade name KRATON®. KRATON® polymers include styrene-diene block copolymers, such as styrene-butadiene, styrene-isoprene, styrene-butadiene-styrene, styrene-isoprene-styrene, and styrene-isoprene/butadiene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These styrenic block copolymers may have a linear, radial or star-shaped molecular configuration. Specific KRATON™ block copolymers include those sold under the brand names G 1652, G 1657, G 1730, MD6673, and MD6973. Various suitable styrenic block copolymers are described in U.S. Pat. No. 4,663,220 to Wisneski, et al., U.S. Pat. No. 4,323,534 to DesMarais, U.S. Pat. No. 4,834,738 to Kielpikowski, et al., U.S. Pat. No. 5,093,422 to Himes, and U.S. Pat. No. 5,304,599 to Himes, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON™. Still other suitable copolymers include the S-I-S and S-B-S elastomeric copolymers, which can be available from Dexco Polymers of Houston, Tex. or TSRC Company of Taiwan under the trade designation VECTOR™. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Of course, other thermoplastic elastomeric polymers may also be used to form the film, either alone or in conjunction with the block copolymers. Semi-crystalline polyolefins, for example, may be employed that have or are capable of exhibiting a substantially regular structure. Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Particularly suitable polyethylene copolymers are those that are "linear" or "substantially linear." The term "substantially linear" means that, in addition to the short chain branches attributable to comonomer incorporation, the ethylene polymer also contains long chain branches in the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/α-olefin copolymer is a function of both the length and amount of the α-olefin. That is, the greater the length of the α-olefin and the greater the amount of α-olefin present, the lower the density of the copolymer. Although not necessarily required, linear polyethylene "plastomers" are particularly desirable in that the content of α-olefin short chain branching content is such that the ethylene copolymer exhibits both plastic and elastomeric characteristics—i.e., a "plastomer." Because polymerization with α-olefin comonomers decreases crystallinity and density, the resulting plastomer normally has a density lower than that of a polyethylene thermoplastic polymer (e.g., LLDPE), which typically has a density (specific gravity) of from about 0.90 grams per cubic centimeter ($g/cm^3$) to about 0.94 $g/cm^3$, but approaching and/or overlapping that of an elastomer, which typically has a density of from about 0.85 $g/cm^3$ to about 0.90 $g/cm^3$, preferably from 0.86 to 0.89. For example, the density of the polyethylene plastomer may be 0.91 $g/cm^3$ or less, in some embodiments from about 0.85 $g/cm^3$ to about 0.90 $g/cm^3$, in some embodiments, from 0.85 $g/cm^3$ to 0.88 $g/cm^3$, and in some embodiments, from 0.85 $g/cm^3$ to 0.87 $g/cm^3$. Despite having a density similar to elastomers, plastomers generally exhibit a higher degree of crystallinity, are relatively non-tacky, and may be formed into pellets that are non-adhesive-like and relatively free flowing. Plastomers also exhibit higher hysteresis/energy loss than styrenic block polymers, for example.

Preferred polyethylenes for use in the present invention are ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from Dow Chemical Company under the designations DOWLEX™ (linear low density polyethylene (LLDPE)) and ATTANE™ (ultralow density polyethylene (ULDPE)). Other suitable ethylene polymers are available from Westlake Chemical Corporation of Houston, Tex. Still other suitable ethylene polymers are described in U.S. Pat. No. 4,937,299 to Ewen, et al., U.S. Pat. No. 5,218,071 to Tsutsui et al., U.S. Pat. No. 5,272,236 to Lai, et al., and U.S. Pat. No. 5,278,272 to Lai, et al., which are incorporated herein in their entirety by reference thereto for all purposes.

Of course, the present invention is by no means limited to the use of ethylene polymers. For instance, propylene plastomers may also be suitable for use in the film. Suitable plastomeric propylene polymers may include, for instance, copolymers or terpolymers of propylene, copolymers of propylene with an α-olefin (e.g., $C_3$-$C_{20}$), such as ethylene, 1-butene, 2-butene, the various pentene isomers, 1-hexene, 1-octane, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, and in some embodiments, from about 2 wt. % to about 10 wt. %. Preferably, the density of the polypropylene (e.g., propylene/α-olefin copolymer) may be 0.91 g/cm$^3$ or less, in some embodiments, from 0.85 g/cm$^3$ to 0.88 g/cm$^3$, and in some embodiments, from 0.85 g/cm$^3$ to 0.87 g/cm$^3$. Suitable propylene polymers are commercially available under the designations VISTAMAXX™ (e.g., 6102), a propylene-based elastomer from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 5,539,056 to Yang, et al., U.S. Pat. No. 5,596,052 to Resconi, et al., and U.S. Pat. No. 6,500,563 to Datta, et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,272,236 to Lai et al., U.S. Pat. No. 5,322,728 to Davis et al., U.S. Pat. No. 5,472,775 to Obijeski et al., U.S. Pat. No. 5,571,619 to McAlpin et al., and U.S. Pat. No. 6,090,325 to Wheat, et al., which are incorporated herein in theft entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have, polydispersity numbers ($M_w/M_n$) of below 4, controlled short chain branching distribution, and controlled isotacticity.

The melt flow index (MI) of the semi-crystalline polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 5000 grams in 10 minutes at 190° C., and may be determined in accordance with ASTM Test Method D1238-E.

The present invention also contemplates the use of thermoplastic polyurethanes as a component of the core layer of the film. Thermoplastic polyurethanes are generally synthesized from a polyol, organic diisocyanate, and optionally a chain extender. The synthesis of such melt-processable polyurethane elastomers may proceed either stepwise (e.g., prepolymer dispensing process) or by simultaneous reaction of all components in a single stage (e.g., one-shot dispensing process) as is known in the art and described in more detail in U.S. Pat. No. 3,963,656 to Meisert, et al., U.S. Pat. No. 5,605,961 to Lee, et al., U.S. Pat. No. 6,008,276 to Kalbe, et al., U.S. Pat. No. 6,417,313 to Kirchmeyer, et al., and U.S. Pat. No. 7,045,650 to Lawrey, et al., as well as U.S. Patent Application Publication Nos. 2006/0135728 to Peerlings, et al. and 2007/0049719 to Brauer, et al., all of which are incorporated herein in their entirety by reference thereto for all purposes.

The thermoplastic polyurethane can typically have a melting point of from about 75° C. to about 250° C., in some embodiments from about 100° C. to about 240° C., and in some embodiments, from about 120° C. to about 220° C. The glass transition temperature ("$T_g$") of the thermoplastic polyurethane may be relatively low, such as from about −150° C. to about 0° C., in some embodiments from about −100° C. to about −10° C., and in some embodiments, from about −85° C. to about −20° C. The melting temperature and glass transition temperature may be determined using differential scanning calorimetry ("DSC") in accordance with ASTM D-3417. Examples of such thermoplastic polyurethanes are available under the designation DESMOPAN™ from Bayer MaterialScience and under the designation ESTANE™ from Lubrizol. DESMOPAN™ DP 9370A, for instance, is an aromatic polyether-based polyurethane formed from poly(tetramethylene ether glycol) and 4,4-methylenebis(phenylisocyanate) ("MDI") and has a glass transition temperature of about −70° C. and a melting temperature of from about 188° C. to about 199° C. ESTANE™ 58245 is likewise an aromatic polyether-based polyurethane having a glass transition temperature of about −37° C. and a melting temperature of from about 135° C. to about 159° C.

The present invention also contemplates the use of thermoplastic ester elastomers and thermoplastic ether elastomers. Of course, besides elastomeric polymers, generally inelastic thermoplastic polymers may also be used so long as they do not adversely affect the elasticity of the laminate. For example, the thermoplastic composition of the core layer may contain other polyolefins (e.g., polypropylene, polyethylene, etc.). In one embodiment, the thermoplastic composition may contain an additional propylene polymer, such as homopolypropylene or a copolymer of propylene. The additional propylene polymer may, for instance, be formed from a substantially isotactic polypropylene homopolymer or a copolymer containing equal to or less than about 10 wt. % of other monomer, i.e., at least about 90% by weight propylene. Such a polypropylene may be present in the form of a graft, random, or block copolymer and may be predominantly crystalline in that it has a sharp melting point above about 110° C., in some embodiments about above 115° C., and in some embodiments, above about 130° C. Examples of such additional polypropylenes are described in U.S. Pat. No. 6,992,159 to Datta, et al., which is incorporated herein in its entirety by reference thereto for all purposes.

b. Skin Layers

As discussed above, it is to be understood that the elastic film of the present invention may be monolayered or multilayered. Multilayered films may be prepared by coextrusion or any other conventional layering technique. When employed, the multilayered film can typically contain at least one thermoplastic skin layer and at least one elastic core layer (as discussed above). For instance, the thermoplastic skin layer(s) may be employed to provide strength and integrity to the resulting multilayered film, while the elastic core layer may be employed to provide elasticity to the multilayered film. In one particular embodiment of the present invention, the film includes at least one elastic core layer positioned between at least two thermoplastic skin layers. In such embodiments, the core layer can provide the desired degree of elasticity to the multilayered film. To impart the desired elastic properties to the film, elastomers can constitute about 55 wt. % or more, in some embodiments about 60 wt. % or more, and in some embodiments, from about 65 wt. % to about 100 wt. % of the polymer content of the elastomeric composition used to form the core layer. In fact, in certain embodiments, the core layer may be generally free of polymers that are inelastic. For example, such inelastic polymers may constitute about 15 wt. % or less, in some embodiments about 10 wt. % or less, and in some embodiments, about 5 wt. % or less of the polymer content of the elastomeric composition.

Meanwhile, although the skin (thermoplastic) layer(s) may possess some degree of elasticity and may, in some embodiments, be formed from any of the materials discussed above, in some embodiments, such layers may be formed from a thermoplastic composition that is less elastic than the elastic layer(s) to ensure that the strength of the film is sufficiently enhanced. For example, one or more elastic layers may be formed primarily from substantially amorphous elastomers (e.g., styrene-olefin copolymers) and one or more thermoplastic layers may be formed from polyolefin plastomers (e.g., single-site catalyzed ethylene or propylene copolymers), which are described in more detail above. Although possessing some elasticity, such polyolefins are generally less elastic than substantially amorphous elastomers. Of course, the thermoplastic layer(s) may contain generally inelastic polymers, such as conventional polyolefins, e.g., polyethylene (low density polyethylene (LDPE), Ziegler-Natta catalyzed linear low density polyethylene (LLDPE), etc.), ultra low density polyethylene (ULDPE), polypropylene, polybutylene, etc.; polytetrafluoroethylene; polyesters, e.g., polyethylene terephthalate (PET), etc.; polyvinyl acetate; polyvinyl chloride acetate; polyvinyl butyral; acrylic resins, e.g., polyacrylate, polymethylacrylate, polymethylmethacrylate, etc.; polyamides, e.g., nylon; polyvinyl chloride; polyvinylidene chloride; polystyrene; polyvinyl alcohol; polyurethanes; polylactic acid; copolymers and mixtures thereof; and so forth. For instance, the skin layers can be formed from one or more ultralow density polyethylenes or linear low density polyethylenes available from Dow Chemical Co. of Midland, Mich. under the designations ATTANE™, such as ATTANE™ 4407, or DOWLEX™, such as DOWLEX™ 2047, 2107, or 2517. Suitable polyethylenes are also available from Westlake Chemical Corp. of Houston, Tex. In certain embodiments, polyolefins (e.g., conventional and/or plastomers) can be employed and constitute about 55 wt. % or more, in some embodiments about 60 wt. % or more, and in some embodiments, from about 65 wt. % to about 100 wt. % of the polymer content of the thermoplastic composition used to form the thermoplastic layer(s). Regardless of the components used in forming the skin layers, the skin layers generally have an elongation at break that is greater than about 300%.

The thickness of the core (elastic) and skin (thermoplastic) layers can be generally selected so as to achieve an appropriate balance between film elasticity and tensile/tear strength. For instance, the thickness of an elastic layer can typically range from about 20 to about 200 micrometers, in some embodiments from about 25 to about 175 micrometers, and in some embodiments, from about 30 to about 150 micrometers. The elastic layer(s) may also constitute from about 70% to about 99.5% of the total thickness of the film, in some embodiments from about 80% to about 99% of the total thickness of the film, and in some embodiments from about 85% to about 95% of the total thickness of the film. On the other hand, the thickness of a thermoplastic layer(s) can typically range from about 0.5 to about 20 micrometers, in some embodiments from about 1 to about 15 micrometers, and in some embodiments, from about 2 to about 12 micrometers. The thermoplastic layer(s) may also constitute from about 0.5% to about 30% of the total thickness of the film, in some embodiments from about 1% to about 20% of the total thickness of the film, and in some embodiments from about 5% to about 15% of the total thickness of the film. In one particular embodiment, an elastic core layer can be sandwiched between two thermoplastic skin layers, where the thickness of each of the skin layers is equal. For example, in one embodiment, the film can include a core layer that constitutes 90% of the total thickness of the film, while the skin layers each constitute 5% of the total thickness of the film. The film may also have a total thickness of from about 20 to about 250 micrometers, in some embodiments, from about 25 to about 225 micrometers, and in some embodiments, from about 30 to about 200 micrometers.

c. Other Film Components

Further, the various layers of the film of the present invention may also contain other components as is known in the art. In one embodiment, for example, one or more of the film layers can include a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. No. 5,932,497 to Morman, et al., U.S. Pat. Nos. 5,997, 981, 6,015,764, and 6,111,163 to McCormack, et al., and U.S. Pat. No. 6,461,457 to Taylor, et al., which are incorporated herein in their entirety by reference thereto for all purposes. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. In certain cases, the filler content of the film may range from about 0.1 wt. % to about 30 wt. %, in some embodiments, from about 0.5 wt. % to about 25 wt. %, and in some embodiments, from about 1 wt. % to about 20 wt. % of the film.

Other additives may also be incorporated into the film, such as melt stabilizers, crosslinking catalysts, pro-rad crosslinking additives, processing stabilizers, heat stabilizers, light stabilizers, antioxidants, heat aging stabilizers, whitening agents, antiblocking agents, bonding agents, tackifiers, viscosity modifiers, etc. Examples of suitable tackifier resins may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS™ previously available from Ciba Specialty Chemicals of Tarrytown, N.Y. and now available from BASF Corporation of Florham Park, N.J.; and DOVERPHOS™ available from Dover Chemical Corp. of Dover, Ohio) are exemplary melt stabilizers. In addition, hindered amine stabilizers (e.g., CHIMASSORB™ available from Ciba Specialty Chemicals) are exemplary heat and light stabilizers. Further, hindered phenols are commonly used as an antioxidant in the production of films. Some suitable hindered phenols include those available from Ciba Specialty Chemicals under the trade name IRGANOX™, such as IRGANOX™ 1076, 1010, or E 201. Moreover, bonding agents may also be added to the film to facilitate bonding of the film to additional materials (e.g., a nonwoven facing). Typically, such additives (e.g., tackifier, antioxidant, stabilizer, etc.) can each be present in an amount from about 0.001 wt. % to about 25 wt. %, in some embodiments, from about 0.005 wt. % to about 20 wt. %, and in some embodiments, from about 0.01 wt. % to about 15 wt. % of the film.

Regardless of the particular film content, the film and/or the materials used to form the film may also be subjected to one or more additional processing steps. In one embodiment, for example, an elastomeric polymer employed in the film can be crosslinked, before, after, and/or during lamination to a nonwoven facing, to provide the film with enhanced elastic characteristics. Crosslinking may be induced by subjecting the polymer to electromagnetic radiation, such as ultraviolet light, electron beam radiation, natural and artificial radio isotopes (e.g., $\alpha$, $\beta$, and $\gamma$ rays), x-rays, neutron beams, positively-charged beams, laser beams, and so forth. The wavelength ("$\lambda$") of the electromagnetic radiation may be about 1000 nanometers or less, in some embodiments about 100 nanometers or less, and in some embodiments, about 1 nanometer or less. Electron beam radiation, for instance, typically has a wavelength of about 1 nanometer or less. The total dosage employed (in one or multiple steps) may likewise range from about 1 megarad (Mrad) to about 30 Mrads, in some embodiments, from about 3 Mrads to about 25 Mrads, and in some embodiments, from about 5 to about 15 Mrads. In addition, the energy level may range from about 0.05 megaelectron volts (MeV) to about 600 MeV. Upon crosslinking, a three-dimensional crosslinked network may be formed that provides the material with additional elasticity in the machine direction, cross-machine direction, or both.

Three-Dimensional Ink Structures

Regardless of the number of layers in the film of the present invention, and regardless of whether or not the film is laminated to a facing as discussed in more detail below, at least one surface of the film can be printed with one or more two-dimensional ink structures that can be activated into three-dimensional ink structures having increased thickness/height, length, and/or width dimensions so as to impart the desired properties to the film. For instance, when the multilayered film is laminated to a facing, the two-dimensional ink structures can be printed onto the outer surface of the film that is not adjacent the facing, such as the skin layer that is not positioned adjacent the facing. On the other hand, when the multilayered film is not laminated to a facing, the ink can be printed onto one or more outer surfaces of the multilayered film, such as one or both skin (thermoplastic) layers, if present.

Desirably, when more than one three-dimensional ink structure is present on a surface of a film, the three-dimensional ink structures generally extend in a predominant direction, such as in the machine direction, cross machine direction, or diagonally in relation to either the machine direction or cross-machine direction, such that a generally continuous linear or curvilinear path or gap where no ink structures are present extends between adjacent three-dimensional ink structures. In other words, a continuous, unidirectional unprinted space exists between adjacent three-dimensional ink structures, such as a linear or curvilinear line or gap, to allow for unidirectional stretching of the film (without the print features significantly impacting the stretchability of the film). By changing the predominant direction in which the three-dimensional ink structures extend, the stretch of the film on which the three-dimensional ink structures are printed can be controlled. Typically, the film can stretch in a direction that is generally perpendicular to the predominant direction of the three-dimensional ink structures. For instance, when the three-dimensional ink structures have a pattern that extends predominantly in the machine direction, the film can be provided with cross-machine direction stretch at the linear or curvilinear path or gap where no three-dimensional ink structures are present. On the other hand, when the three-dimensional ink structures have a pattern that extends predominantly in the cross-machine direction, the film can be provided with machine direction stretch at the linear or curvilinear path or gap where no three-dimensional ink structures are present.

Any ink that is three-dimensional, or that is two-dimensional and can be activated or treated such that it is rendered three-dimensional, can be applied to the films discussed above in various three-dimensional ink structure patterns. The one or more three-dimensional ink structures present on the film may be liquid pervious, semi-pervious, or liquid impervious, and may be absorbent or nonabsorbent, as desired. Further, although the three-dimensional ink structures expand in the height (e.g., the z-direction) and length and width directions (e.g., either the machine direction or cross-machine direction) when compared to the two-dimensional ink structures, even after activation or expansion, the original spacing between adjacent two-dimensional ink structures is such that a continuous gap or path exists between adjacent three-dimensional ink structures.

Figure 2A:
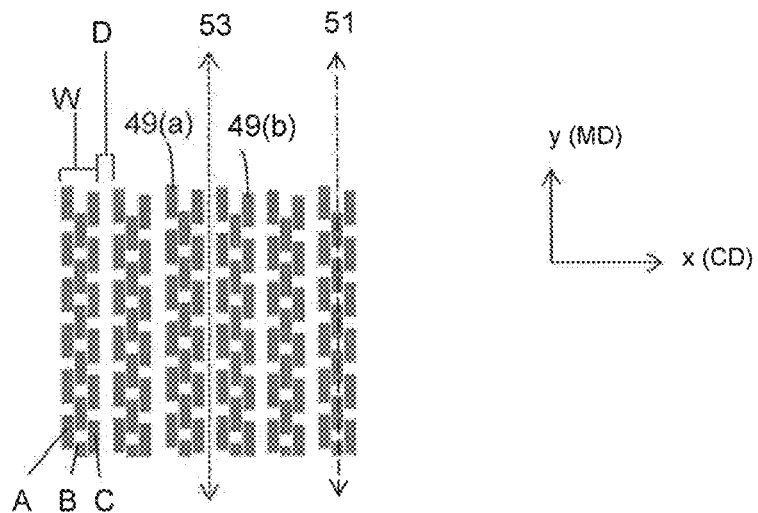
FIG. 2A illustrates one embodiment of an ink pattern that can be applied to an outer surface of an elastic film of the present invention before activation when the ink is two-dimensional.

In one particular embodiment, as shown in FIG. 2A, two dimensional ink structures 49a and 49b are printed that extend in a predominant direction that is generally linear, which, in the particular embodiment of FIG. 2A, extends in the machine direction. The two dimensional ink structures 49a and 49b having a width W in the cross-machine direction can each be separated by a generally continuous linear path or gap 53 spanning a distance D in the cross-machine direction that generally follows the predominant direction 51 of the two dimensional ink structures 49a and 49b, which, in the particular embodiment of FIG. 2A, is the machine direction. As such, the direction of stretch of the film can be generally perpendicular to the predominant direction 51 (i.e., generally the cross-machine direction) of the two-dimensional ink structures 49a and 49b at gap 53. As shown in FIG. 2A, each of the two-dimensional ink structures 49a and 49b can comprise individual, discrete shapes such as three rows of repeating geometric shapes (here, rectangles A, B, and C) that are each separated by a gap, where such gap closes and becomes imperceptible once the two-dimensional ink structures 49a and 49b are activated into three-dimensional ink structures 50a and 50b as shown in FIG. 2B.

Figure 2B:
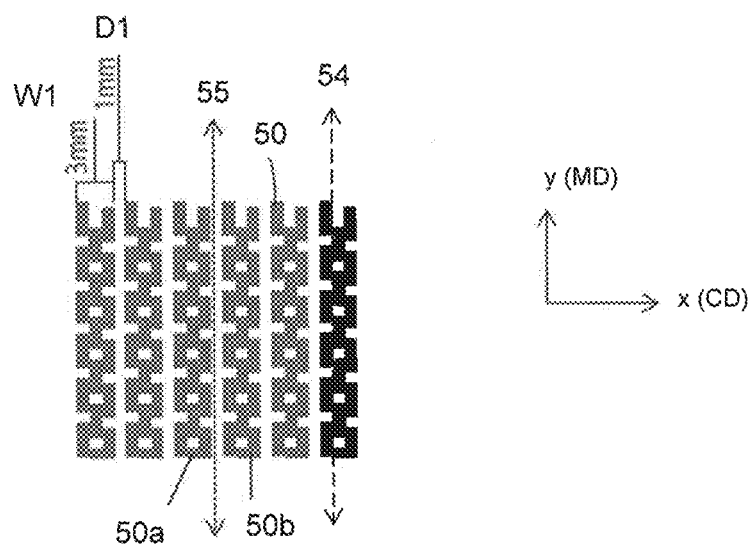
FIG. 2B illustrates one embodiment of an ink pattern that can be applied to an outer surface of an elastic film of the present invention after the ink has been rendered three-dimensional.

Once activated by heat, ultraviolet treatment, or any other suitable means, the two-dimensional ink structures 49a and 49b can be rendered three-dimensional ink structures 50a and 50b as shown in FIG. 2B. The two-dimensional ink structures 49a and 49b of FIG. 2A can expand and fill such that any individual components are not perceptible, although it is to be understood that in some embodiments, the individual components (e.g., rectangles) of two-dimensional ink structures 49a and 49b may still be perceptible after activation. The three-dimensional ink structures 50, 50a, and 50b of FIG. 2B having a width W1 in the cross-machine direction can each be separated by a generally continuous path or gap 55 spanning a distance D1 in the cross-machine direction that generally follows the predominant direction of the three dimensional ink structures 50, 50a, and 50b, which, in the particular embodiment of FIG. 2A, is the machine direction. As such, the direction of stretch of the film can be generally perpendicular to the direction of the gap 55 such that the direction of stretch can generally be the cross-machine direction. Due to expansion upon activation, the width W1 of and the distance D1 spanned by the three-dimensional ink structures 50, 50a, and 50b in FIG. 2B can increase compared to the width W and distance D of the two-dimensional ink structures 49a and 49b of FIG. 2A.

As shown in FIGS. 2A-11, the two-dimensional ink structures 49a and 49b and three-dimensional ink structures 50, 50a, and 50b, for example, can take the form of any suitable pattern, such as a continuous or discontinuous pattern, and can be disposed at various locations on an outer surface of the film, such as a skin layer 10a, if present. For instance, in FIGS. 2A-5 and 7, the three-dimensional ink structures 50 are in the form of numerous continuous, segmented lines or strips, while in FIG. 8, the three-dimensional ink structures 50 are in the form of individual, discrete dots.

Figure 7:
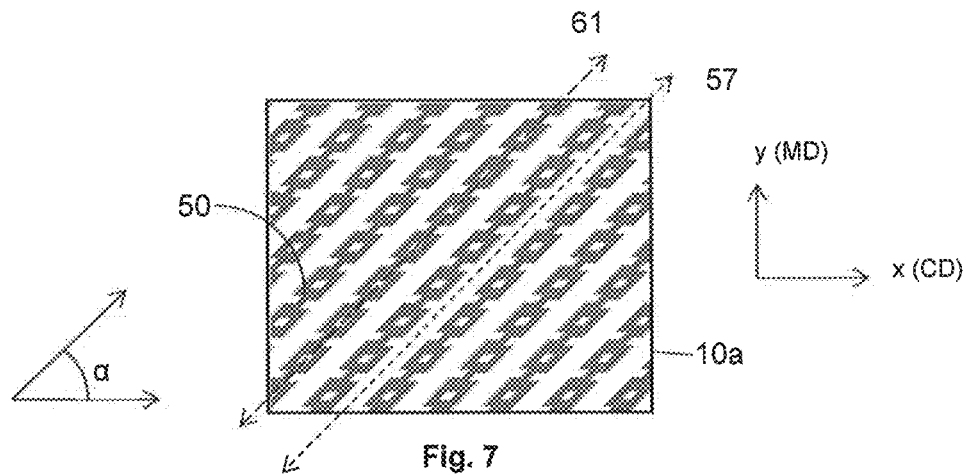
FIG. 7 illustrates a top view of another embodiment of an elastic film of the present invention to which an ink pattern has been applied after the ink has been rendered three-dimensional.
Figure 8:
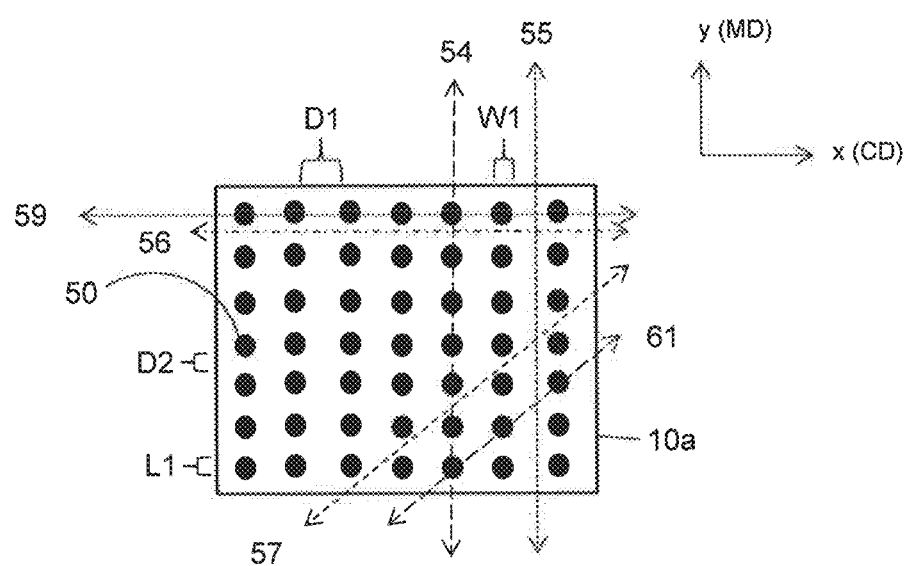
FIG. 8 illustrates a top view of another embodiment of an elastic film of the present invention to which an ink pattern has been applied after the ink has been rendered three-dimensional.
Figure 9:
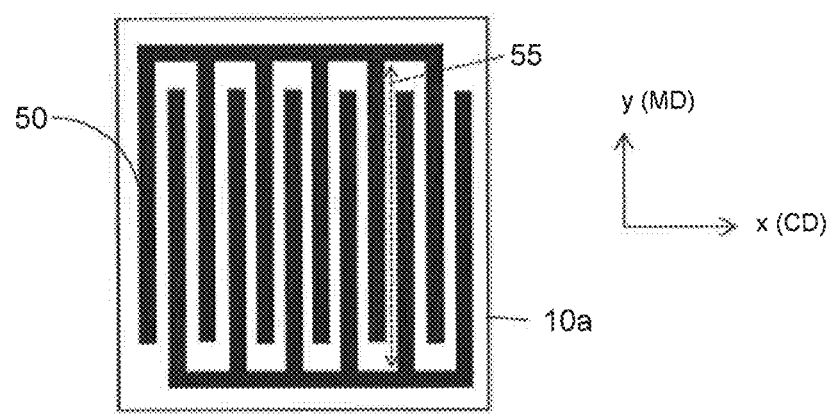
FIG. 9 illustrates a top view of another embodiment of an elastic film of the present invention to which an ink pattern has been applied after the ink has been rendered three-dimensional.
Figure 10:
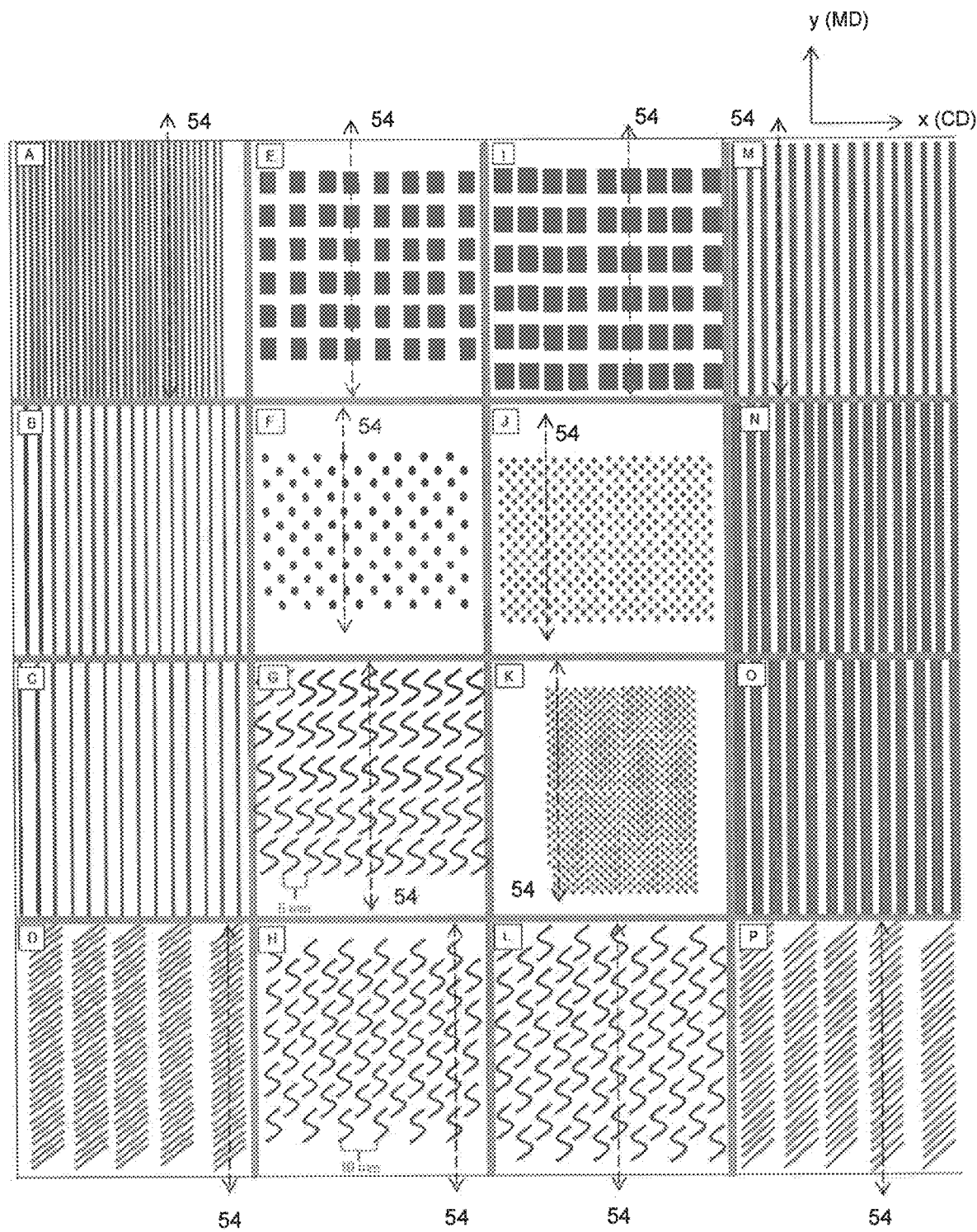
FIGS. 10A-10P illustrate various top views of an elastic film of the present invention to which various ink patterns have been applied after the ink has been rendered three-dimensional.

As shown in FIG. 8, the three-dimensional ink structures can be defined by a width W1 in the x-direction (cross-machine direction) and a length L1 in the y-direction (machine direction). In addition, the three-dimensional ink structures can be separated in the x-direction (cross-machine direction) by a distance D1 and in the y-direction (machine direction) by a distance D2. These dimensions can vary depending on the desired stretch properties, rip or tear properties, and aesthetic properties of the resulting elastic film on which the three-dimensional structures are disposed. Using the pattern of FIG. 8 as a reference example, in one embodiment, the width W1 in the x-direction (cross-machine direction) of a three-dimensional ink structure 50 can range from about 0.25 mm to about 25 mm, such as from about 0.5 mm to about 20 mm, such as from about 0.75 mm to about 15 mm. Further, the x-direction (cross-machine direction) distance D1 between each of the three dimensional ink structures 50 can range from about 0.5 mm to about 20 mm, such as from about 0.75 mm to about 15 mm, such as from about 1 mm to about 10 mm. Meanwhile, the length L1 in the y-direction (machine direction) of a three-dimensional ink structure 50 can range from about 0.5 mm to about 20 mm, such as from about 0.75 mm to about 15 mm, such as from about 1 mm to about 10 mm. In addition, the y-direction (machine direction) distance D2 between each of the three dimensional ink structures 50 can range from about 0.5 mm to about 20 mm, such as from about 0.75 mm to about 15 mm, such as from about 1 mm to about 10 mm. Although discussed above in reference to FIG. 8, it is also to be understood that such spacing and dimensions can apply to any of the patterns shown in FIGS. 2A-7, 9, 10A-10P, and 11.

In addition, as shown in FIG. 8, when a pattern of discrete dots is utilized, the three-dimensional ink structures 50 can extend in a predominant direction 54 that is generally aligned with the y-direction (machine direction), where the three-dimensional ink structures 50 are separated by a path or gap 55 that also generally follows the y-direction (machine direction). On the other hand, it can also be said that the three-dimensional ink structures 50 can extend in a predominant direction 59 that is generally aligned with the x-direction (cross-machine direction), where the three-dimensional ink structures 50 are separated by a path or gap 56 that also generally follows the x-direction (cross-machine direction). Meanwhile, it can also be said that the three-dimensional ink structures 50 can extend in a predominant direction 61 that is diagonal from either the y-direction (machine direction) or x-direction (cross-machine direction), where the three-dimensional ink structures 50 are separated by a path or gap 57 that is diagonal from either the y-direction (machine direction) or x-direction (cross-machine direction). In any event, the pattern of dots can be arranged to promote stretching of the film in the paths or gaps 55, 56, and 57.

Figure 5:
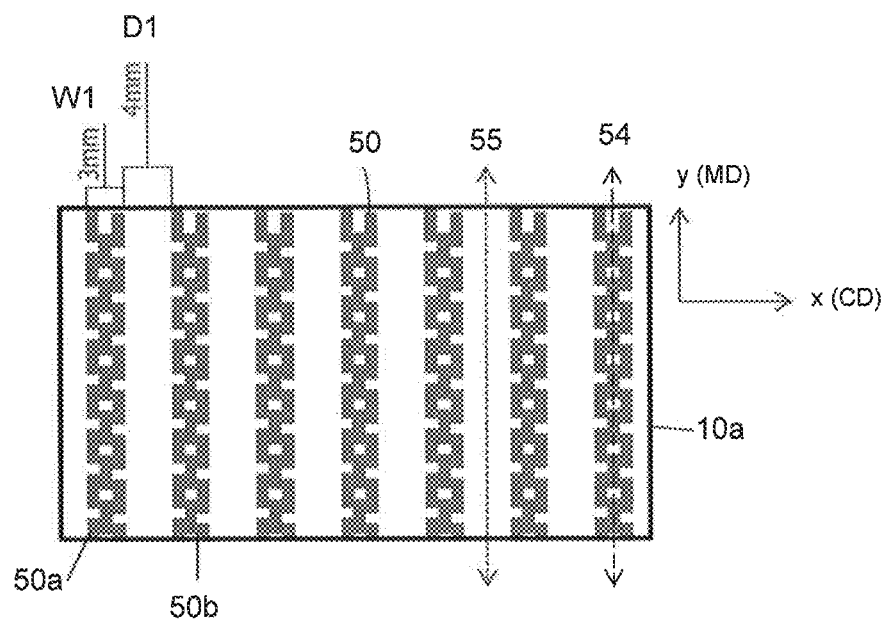
FIG. 5 illustrates a top view of one embodiment of an elastic film of the present invention to which an ink pattern has been applied in the machine direction after the ink has been rendered three-dimensional.

Further, the three-dimensional ink structures 50, when in the form of continuous lines or strips as shown in FIGS. 5 and 7, can be oriented at various angles in relation to the x-direction (cross-machine direction) of the film. For instance, as shown in FIG. 5, the three-dimensional ink structures 50 can be positioned generally perpendicular, or at a 90° angle, to the x-direction (cross-machine direction) of the film, such that it is generally aligned with the y-direction (machine direction) of the film in a predominant direction 54 with a gap 55 between adjacent three-dimensional ink structures 50. Meanwhile, as shown in FIG. 7, in other embodiments, the three-dimensional ink 50 can be positioned at an angle that is about 45° relative to the x-direction (cross-machine direction) in a predominant direction 61 with a gap 57 between adjacent three-dimensional ink structures 50. Generally, the angle α at which the three-dimensional ink 50 is positioned relative to the x-direction (cross-machine direction) of the film can range from about 15° to about 90°, such as from about 20° to about 85°, such as from about 25° to about 75°. Depending on the arrangement of the three-dimensional structures and their pattern of application, tearing or ripping of the film or laminate can be prevented at certain desired locations while being promoted at certain other desired locations on the film or laminate.

Figure 3:
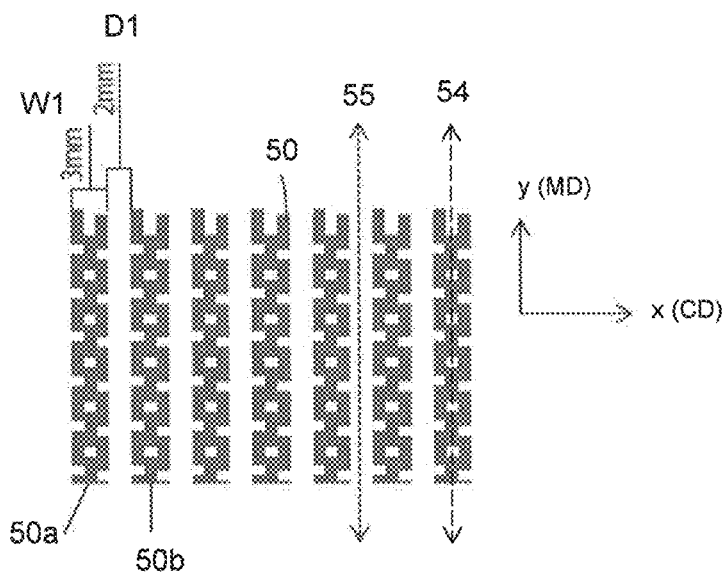
FIG. 3 illustrates another embodiment of an ink pattern that can be applied to an outer surface of an elastic film of the present invention after the ink has been rendered three-dimensional.
Figure 4:
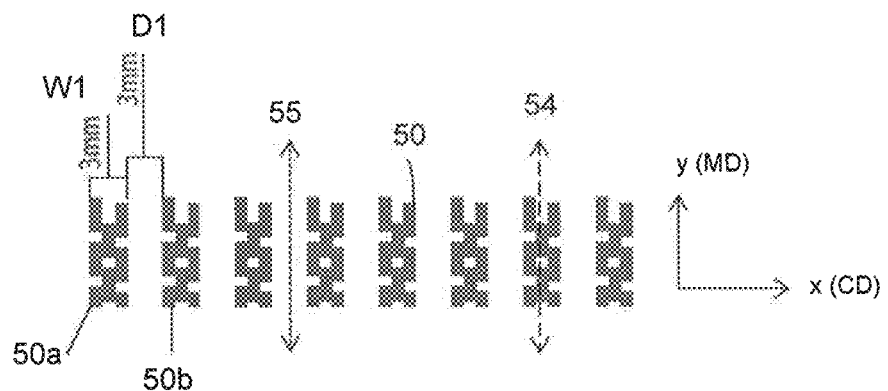
FIG. 4 illustrates still another embodiment of an ink pattern that can be applied to an outer surface of an elastic film of the present invention after the ink has been rendered three-dimensional.

Meanwhile, as shown in FIGS. 2B, 3, 4, and 5, the width W1 of the three-dimensional ink structures 50 in the x-direction (cross-machine direction) can be about 3 mm in some embodiments. Further, as shown in FIG. 2B, the distance D1 between a first three-dimensional ink structure 50a and a second three-dimensional ink structure 50b can, in one embodiment, be about 1 mm. Further, FIG. 3 shows that the distance D1 between a first three-dimensional ink structure 50a and a second three-dimensional ink structure 50b is about 2 mm. As shown in FIG. 4, in another embodiment, the distance D1 between a first three-dimensional ink structure 50a and a second three-dimensional ink structure 50b can be about 3 mm. Further, as shown in FIG. 5, the distance D1 between a first three-dimensional ink structure 50a and a second three-dimensional ink structure 50b can be about 4 mm in one embodiment. Regardless of the distance D1 between a first three-dimensional ink structure 50a and a second three-dimensional ink structure 50b, the distance should be large enough such that upon expansion of the three-dimensional ink structures 50a and 50b upon activation of the two-dimensional ink, a large enough gap 55 exists between the three-dimensional ink structures 50a and 50b so that the stretch properties of the film are not negatively impacted by the three-dimensional ink structures 50a and 50b. In addition, the three-dimensional ink structures 50 can extend any length in the y-direction (machine direction), which can depend on the size of the article in which the film or laminate on which such structures are printed is employed. Further, it is to be understood that the three-dimensional ink structures 50 extend in a predominant direction 54 in the y-direction (machine direction) such that a generally continuous linear path or gap 55 exists between adjacent three-dimensional ink structures 50 in the y-direction (machine direction) such that the film is exposed at the gap 55 to enhance the stretch properties of the film at a direction that can be generally perpendicular to the predominant direction 54 of the three-dimensional ink structures 50.

Additional configurations or patterns for the three-dimensional ink structures are shown in FIGS. 10A-10P and are discussed in more detail below, although it is to be understood that the patterns of the three-dimensional ink structures are not drawn to scale. For instance, FIG. 10A represents multiple 3 mm wide three-dimensional ink structures in the form of parallel lines extending in a predominant direction 54 in the y-direction (machine direction) with an x-direction (cross-machine direction) distance of 2 mm between them. Meanwhile, FIG. 10B shows multiple 3 mm wide three-dimensional ink structures in the form of parallel lines extending in a predominant direction (not labeled but the same as that of FIG. 10A) in the y-direction (machine direction) with an x-direction (cross-machine direction) distance of 4 mm between them, and FIG. 10C shows multiple 3 mm wide three-dimensional ink structures in the form of parallel lines extending in a predominant direction (not labeled but the same as that of FIG. 10A) in the y-direction (machine direction) with an x-direction (cross-machine direction) distance of 6 mm between them.

Furthermore, FIG. 10D shows five groups of three-dimensional ink structures extending in a predominant direction 54 in the y-direction (machine-direction), each group comprising 2 mm wide lines rotated at a 45° angle with respect to the x-direction (cross-machine direction) with a distance of 2 mm between each line in each of the groups and an x-direction (cross-machine direction) distance of 5 mm between the groups of three-dimensional ink structures.

Meanwhile, FIG. 10E shows 8 groups of three-dimensional ink structures extending in a predominant direction 54 in the y-direction (machine direction), each group comprising 4 mm wide (x-direction) by 5 mm tall (y-direction) rectangles with a y-direction (machine direction) distance of 3 mm between each of the rectangles in each of the groups and an x-direction (cross-machine direction) distance of 3 mm between the groups of the three-dimensional ink structures.

Moreover, FIG. 10F shows 3 mm diameter circular dots with an x-direction (cross-machine direction) distance of 4 mm between them and a y-direction (machine direction) distance of 8 mm between them. As shown, the predominant direction 54 of the dots can generally extend in the y-direction (machine direction), although it is to be understood that the predominant direction of the dots could also extend in the x-direction (cross-machine direction) or diagonally in relation to the y-direction (machine direction) or x-direction (cross-machine direction). Further, every other column of dots in the y-direction (machine direction) is shifted vertically in the y-direction (machine direction) by 4 mm to create a staggered pattern.

Additionally, FIG. 10G shows 12 groups of three-dimensional ink structures comprising multiple, angled S-shaped three-dimensional ink structures formed from lines having a width of 2 mm such that the length of each S in the y-direction (machine direction) is 9 mm and the overall width of each S in the x-direction (cross-machine direction) is 4 mm. The predominant direction 54 of each of the groups can generally extend in the y-direction (machine direction) as shown and can also extend in the cross-machine direction based on the alignment of the S-shaped structures. Further, the x-direction (cross-machine direction) distance between each group of S-shaped three-dimensional ink structures is 5 mm and the y-direction (machine direction) distance between each S in each of the groups is 3 mm.

Similarly, FIG. 10H shows 12 groups of three-dimensional ink structures comprising multiple, angled S-shaped three-dimensional ink structures formed from lines having a width of 2 mm such that the length of each S in the y-direction (machine direction) is 9 mm and the overall width of each S in the x-direction (cross-machine direction) is 4 mm. The predominant direction 54 of each of the groups generally extends in the y-direction (machine direction) as shown and can also extend diagonally from the cross-machine direction based on the alignment of the S-shaped structures. Further, the x-direction (cross-machine direction) distance between each S is 10 mm and the y-direction (machine direction) distance between each S is 3 mm. In addition, every other column of Ss is shifted or staggered vertically in the y-direction (machine direction) by 3 mm.

FIG. 10I shows 9 groups of three-dimensional ink structures extending in a predominant direction 54 in the y-direction (machine direction), each group comprising 4 mm wide (x-direction) by 5 mm tall (y-direction) rectangles with a y-direction (machine direction) distance of 6 mm between each of the rectangles in each of the groups and an x-direction (cross-machine direction) distance of 6 mm between the groups of the three-dimensional ink structures.

FIG. 10J shows 2 mm diameter circular dots with an x-direction (cross-machine direction) distance of 4 mm between them and a y-direction (machine direction) distance of 8 mm vertical between them. Further, every other column of dots in the y-direction (machine direction) is shifted vertically in the y-direction (machine direction) by 4 mm to create a staggered pattern. As shown, the predominant direction 54 of the dots can generally extend in the y-direction (machine direction), although it is to be understood that the predominant direction of the dots could also extend in the x-direction (cross-machine direction) or diagonally in relation to the y-direction (machine direction) or x-direction (cross-machine direction). Meanwhile, FIG. 10K shows 1 mm diameter circular dots with an x-direction (cross-machine direction) distance of 2 mm between them and a y-direction (machine direction) distance of 4 mm vertical between them. Further, every other column of dots in the y-direction (machine direction) is shifted vertically by 2 mm to create a staggered pattern. As shown, the predominant direction 54 of the dots can generally extend in the y-direction (machine direction), although it is to be understood that the predominant direction of the dots could also extend in the x-direction (cross-machine direction) or diagonally in relation to the y-direction (machine direction) or x-direction (cross-machine direction).

Also, FIG. 10L shows 12 groups of three-dimensional ink structures comprising multiple, angled S-shaped three-dimensional ink structures formed from lines having a width of 2 mm such that the height of each S in the y-direction (machine direction) is 9 mm and the overall width of each S in the x-direction (cross-machine direction) is 4 mm. The predominant direction 54 of each of the groups generally extends in the y-direction (machine direction) as shown and can also extend diagonally from the cross-machine direction based on the alignment of the S-shaped structures. Further, the x-direction (cross-machine direction) distance between each S is 5 mm and the y-direction (machine direction) distance between each S is 9 mm. In addition, every other column of Ss is shifted or staggered vertically in the y-direction (machine direction) by 4.5 mm.

Further, FIG. 10M shows multiple 6 mm wide three-dimensional ink structures in the form of parallel lines extending in a predominant direction 54 in the y-direction (machine direction) with a x-direction (cross-machine direction) distance of 2 mm between them, FIG. 10N shows multiple 9 mm wide three-dimensional ink structures in the form of parallel lines extending in a predominant direction (not labeled but the same as that of FIG. 10M) in the y-direction (machine direction) with a x-direction (cross-machine direction) distance of 2 mm between them, and FIG. 10O shows multiple 12 mm wide three-dimensional ink structures in the form of parallel lines extending in a predominant direction (not labeled but the same as that of FIG. 10M) in the y-direction (machine direction) with a x-direction (cross-machine direction) distance of 2 mm space between them.

FIG. 10P shows five groups of three-dimensional ink structures extending in a predominant direction 54 in the y-direction (machine-direction), each group comprising 2 mm wide lines rotated at a 45° angle with respect to the x-direction (cross-machine direction) with a distance of 3 mm between each line in each of the groups and an x-direction (cross-machine direction) distance of 5 mm between groups of three-dimensional ink structures.

Figure 11:
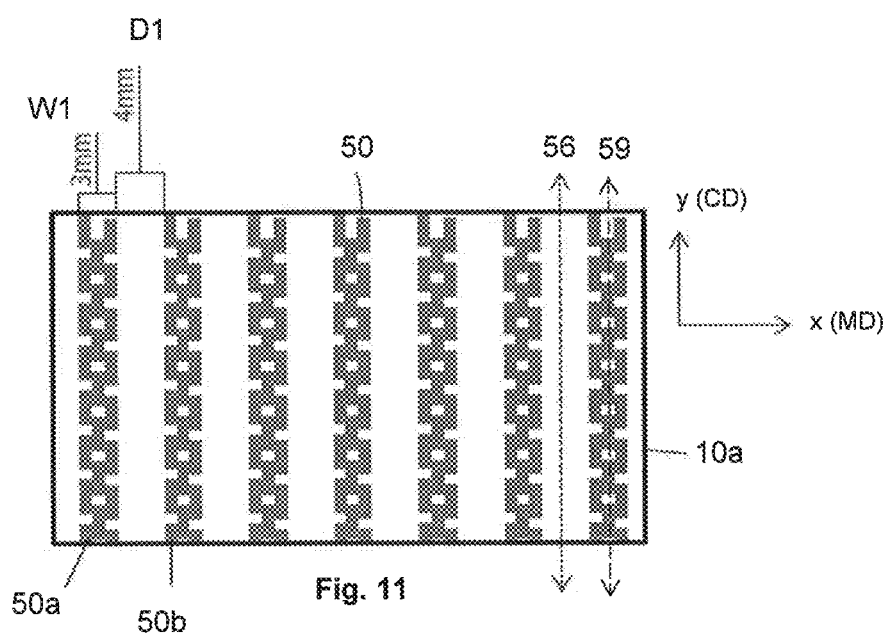
FIG. 11 illustrates a top view of one embodiment of an elastic film of the present invention to which an ink pattern has been applied in the cross-machine direction after the ink has been rendered three-dimensional.

Moreover, although the three-dimensional ink structures 50 are shown and discussed above as being printed to have a predominant direction 54 that generally extends along the y-direction (machine direction) of the film, it is also to be understood that the three-dimensional ink structures 50 can be printed generally along the cross-machine direction of the film. For instance, as shown in FIG. 11 the three-dimensional ink structures 50 are shown as being printed to have a predominant direction 56 that generally extends along the x-direction (cross-machine direction) of the film, where the three-dimensional ink structures 50 are separated by a path or gap 56 that also generally follows the x-direction (cross-machine direction). Because the three-dimensional ink structures 50 have a pattern that extends predominantly in the cross-machine direction, the film can be provided with machine direction stretch at the linear path or gap 56 where no three-dimensional ink structures are present.

Suitable materials for the three-dimensional ink structures 50 include heat-activatable expandable inks, such as AQUA-PUFF™ inks obtainable from Polytex Environmental Inks (Bronx, N.Y.), including MW 4319, MW 4404, MW 4870, and 12.1A. Such inks are available in numerous colors including blue, green, and white. In some embodiments of the present disclosure, for example, white puff inks can be printed on a film surface to create an illusion that a nonwoven facing is present on the film surface rather than a printed ink. Other commercially available inks are available from Eastern Color and Chemical Company (Greenville, S.C.), International Coatings Company (Cerritos, Calif.), Dongguan City Haiya Printing Material Company (China), Atlas Screen Supply Company (Schiller Park, Ill.), NEHOC Australia Pty, Limited (Australia), and INX International Ink Corporation (Schaumburg, Ill.). Such inks are expandable inks which react when exposed to heat to produce a reaction that causes the ink to expand or "puff" into a three-dimensional structure. The inks may include additives, known in the art as blowing agents, and include chemicals which undergo physical or chemical changes on heating to form a gaseous product. Such additives include EXPANCEL™ 461 DU Microsphere (supplied by Expancel), Unicell OH (supplied by OMYA), and Genitron LE (supplied by Acrol) or other gas-encapsulated thermoplastic microspheres. The printing of such inks can occur at a number of steps in the converting process, such as on an off-line printing step, or on-line during the product assembly process. Further, the ink can be printed at one process step, and expanded by heat activation at a downstream step.

In some embodiments, the three-dimensional ink structures 50 can include an optional amount of moisture absorbing polymer. The polymer can be present in the three-dimensional structures 50 in an amount as desired. For example, in some aspects, the three-dimensional structures 50 can contain up to about 1 wt. %, such as up to about 5 wt. %, or even up to about 10 wt. % or more moisture absorbing polymer to provide improved benefits. Examples of suitable moisture absorbing polymers include, but are not limited to, polyethylene oxide, polyethylene glycol, polyvinyl alcohol, polyvinyl pyrolidone, polyvinyl pyridine, or mixtures thereof.

In some embodiments, the three-dimensional ink structures 50 can include an optional elastomeric polymer. The elastomeric polymer may have permeability for water vapor which can facilitate moisture absorption. Further, the elastomeric polymer may add resilience or flexibility to the three-dimensional ink structures 50. The elastomeric polymer component can be present in an amount which is effective to achieve the desired dimensional change properties. For example, the three-dimensional ink structures 50 can contain up to about 1 wt. %, such as up to about 5 wt. %, or even up to about 10 wt. % or more elastomeric polymer to provide improved benefits. Examples of suitable elastomeric polymers include, but are not limited to, thermoplastic polyurethanes, poly(ether-amide) block copolymers, thermoplastic rubbers such as uncrosslinked polyolefins, styrene-butadiene copolymers, silicon rubbers, synthetic rubbers such as nitrile rubber, styrene isoprene copolymers, styrene ethylene butylenes copolymers, butyl rubber, nylon copolymers, spandex fibers comprising segmented polyurethane, ethylene-vinyl acetate copolymer or mixtures thereof.

Additionally, adhesion promoters can be added to the three dimensional ink structures 50. For example, Carboset 514H, available commercially from Noveon, Inc. of Cleveland, Ohio, is an acrylic colloidal dispersion polymer supplied in ammonia water, which can dry to a clear, water-resistant, non-tacky thermoplastic film.

In addition, the three-dimensional ink structures 50 can generally contain a coloring agent (e.g., pigment or dye), a solvent, and any other desired ingredients. Typically, a pigment refers to a colorant based on inorganic or organic particles which do not dissolve in water or solvents. Usually pigments form an emulsion or a suspension in water. On the other hand, a dye generally refers to a colorant that is soluble in water or solvents.

The pigment or dye in the three-dimensional ink 50 can be present in an amount effective to be visible once applied to the elastic film 10. For example, the pigment or dye can be present in the ink composition at a concentration between about 0.25% to about 40% based on the dry weight basis, and preferably between greater than or equal to about 1% and less than or equal to about 10%.

Suitable organic pigments, include dairylide yellow AAOT (for example, Pigment Yellow 14 CI No. 21 095), dairylide yellow AAOA (for example, Pigment Yellow 12 CI No. 21090), Hansa Yellow, CI Pigment Yellow 74, Phthalocyanine Blue (for example, Pigment Blue 15), lithol red (for example, Pigment Red 52:1 CI No. 15860:1), toluidine red (for example, Pigment Red 22 CI No. 12315), dioxazine violet (for example, Pigment Violet 23 CI No. 51319), phthalocyanine green (for example, Pigment Green 7 CI No. 74260), phthalocyanine blue (for example, Pigment Blue 15 CI No. 74160), naphthoic acid red (for example, Pigment Red 48:2 CI No. 15865:2). Inorganic pigments include titanium dioxide (for example, Pigment White 6 CI No. 77891), carbon black (for example, Pigment Black 7 CI No. 77266), iron oxides (for example, red, yellow, and brown), ferric oxide black (for example, Pigment Black 11 CI No. 77499), chromium oxide (for example, green), ferric ammonium ferrocyanide (for example, blue), and the like.

Suitable dyes that may be used include, for instance, acid dyes, and sulfonated dyes including direct dyes. Other suitable dyes include azo dyes (e.g., Solvent Yellow 14, Dispersed Yellow 23, and Metanil Yellow), anthraquinone dyes (e.g., Solvent Red 111, Dispersed Violet 1, Solvent Blue 56, and Solvent Orange 3), xanthene dyes (e.g., Solvent Green 4, Acid Red 52, Basic Red 1, and Solvent Orange 63), azine dyes (e.g., Jet Black), and the like.

The three-dimensional ink structures 50 can be applied to an outer surface of the film 10 while generally dispersed or dissolved in a low viscosity carrier. Exemplary solvents are aliphatic hydrocarbons with common binder types, such as polyamide, shellac, nitro-cellulose, and styrene-maleic. Generally, solvent-based treatments include non-catalytic, block urethane resin, which generally demonstrate superior durability over traditional flexographic binders, such as styrene-maleic, rosin-maleic, and acrylic solutions. Desired solvent blends include various acetates such as ethyl acetate, N-propyl acetate, isopropyl acetate, isobutyl acetate, N-butyl acetate, and blends thereof; various alcohols including ethyl alcohol, isopropyl alcohol, normal propyl alcohol, and blends thereof; and glycol ethers including EKTASOLVE™, EP (ethylene glycol monopropyl ether), EB (ethylene glycol monobutyl ether), DM (diethylene glycol monomethyl ether), DP (diethylene glycol monopropyl ether), and PM (propylene glycol monomethyl ether), which may be obtained from Eastman Chemical of Kingsport, Tenn. Other glycols that may also be used are DOWANOL™ obtainable from Dow Chemical of Midland, Mich. A desired solvent blend may be a blend of about 50 percent to about 75 percent glycol ether, about 25 percent to about 35 percent N-propyl acetate, and about 15 percent to about 25 percent N-butyl acetate.

Suitable water-based three-dimensional ink structures 50 that may be used may further include emulsions that may be stabilized in water-ammonia and may further comprise alcohols, glycols, or glycol ethers as co-solvents. Generally, organic solvents (less than or equal to about 7 wt. %) may be added to water-based treatments: alcohols, for example, propan-2-ol may be added for speeding up drying and assisting wetting, glycols, for example, mono propylene glycol to slow down drying, glycol ethers, for example, dipropyl glycol mono methyl ether to aid film formation. Such solvents may be commodity chemicals, commercially available from various companies. Generally, water-based treatments include self-crosslinking acrylic copolymer emulsion, which may have demonstrated superior durability over traditional non-crosslinking binders such as acrylic solutions and dispersion copolymers. Besides the solvent and pigments, the heat-activatable expandable treatment may comprise a binder. The binder helps stabilize the pigment onto the film. Generally, the pigment-to-binder ratio is typically from 1:20 to 1:2.

Waxes may also be included in the three-dimensional ink structures 50 to increase the slip and improve the rub-resistance of the structures. Common classifications of waxes include animal (for example, beeswax and lanolin), vegetable (for example, carnauba and candellilia), mineral (for example, paraffin and microcrystalline), and synthetic (for example, polyethylene, polyethylene glycol, and TEFLON™). In one embodiment, a wax can be present in an amount of about 0.5 wt. % to about 5 wt. % based on the total weight of the three-dimensional ink structure formulation.

It is to be understood that additional, or multiple, three-dimensional ink structures can each comprise the same material, or they can comprise different materials. As such inks are available in a variety of colors, in some embodiments the inks may be used to additionally provide a visually distinctive multi-color pattern or appearance to the product. Changes to these patterns and colors could be as easy as changing the ink and printing plate, such as a printing plate used in flexographic printing.

After drying or concurrent with drying, the two dimensional ink structures 49 are capable of being activated into three-dimensional ink structures 50 having a desired shape and spacing between them upon application of sufficient heat or ultraviolet treatment to the structures. For instance, the three dimensional ink structures 50, upon exposure to heat, will expand or grow in size. Application of the heat may occur by any suitable means, such as for example, treatment with a hot air stream, passing through a heat tunnel, contact with a hot surface, e.g., a steam can, iron, and so forth, treatment with infrared radiation, treatment with microwaves, ultraviolet treatment, and so forth.

Suitably, the three-dimensional ink structures are capable of expanding in volume by greater than about 1000%, or greater than about 2000%, or greater than about 3000%. As further examples, the three-dimensional ink structures may be capable of expanding in volume from about 100% to about 6000%, or from about 500% to about 5000%, or from about 1000 to about 4500%.

Figure 6:
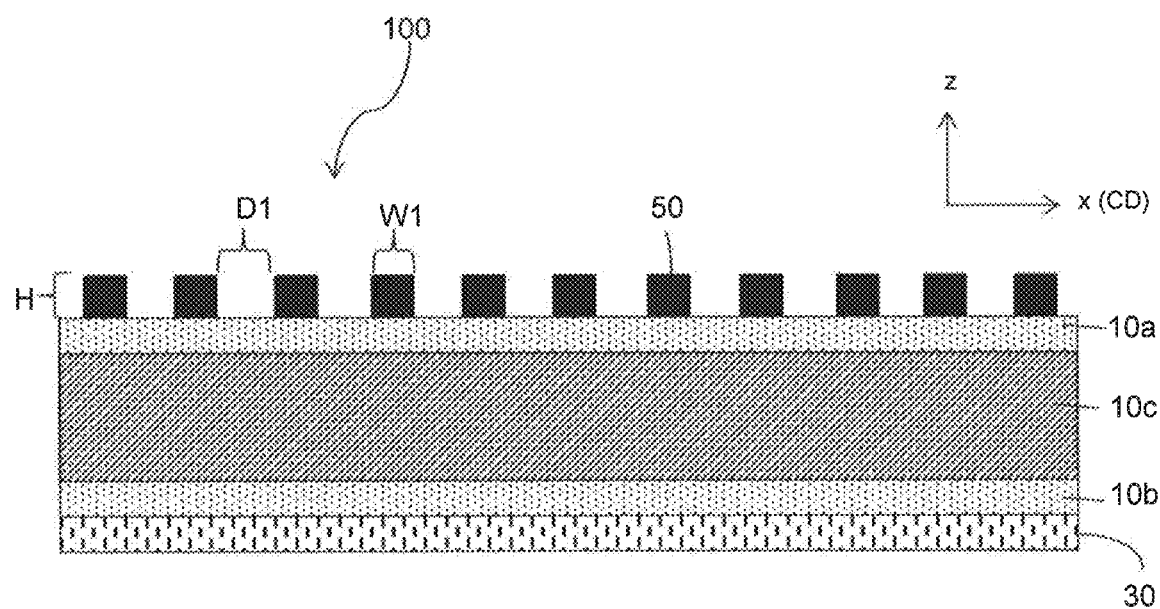
FIG. 6 is a cross-sectional view illustrating an elastic laminate having a an ink applied to at least one surface, as contemplated by one embodiment of the present invention after the ink has been rendered three-dimensional.

When heat is applied to the three-dimensional ink structures, the three-dimensional ink structures expand in volume, rising to a height/thickness H in the z-direction and a width W1 in the x-direction (cross-machine direction), with a gap D1 between adjacent three-dimensional ink structures 50, as shown in FIG. 6. It should be understood that because the gap D1 shrinks upon activation of the two-dimensional ink into a three-dimensional ink structure, this shrinkage of the gap should be taken into account when selecting the desired ink placement and gap sizes desired after activation. The height H will vary as desired, and will vary with various structure designs. For example, the height H that a given three-dimensional ink structure 50 will expand can be at least about 0.01 mm, such as at least about 0.025 mm, such as at least about 0.05 mm or more to provide improved benefits. As further examples, the three-dimensional ink structures 50 may have a height or thickness from about 0.01 mm to about 5 mm, such as from about 0.025 mm to about 4 mm, such as from about 0.05 mm to about 3 mm. The distance of expansion can be modified as desired according to several factors, including the expanding ability of the three-dimensional ink structures, the temperature reached, and the amount of time the material is heated and so forth. In one aspect, different three-dimensional ink structures applied to the film may be constructed of different expandable materials to create three-dimensional ink structures of varying height.

Further, it is to be understood that as the desired height or thickness of the three-dimensional ink structures 50 increases, the pre-activated gap 53 between the original two-dimensional ink structures 49a and 49b should also be increased so that a gap 55 will still exist between three-dimensional ink structures 50a and 50b once activated, as shown in FIGS. 2A and 2B. Moreover, in some embodiments, the three-dimensional ink structures 50, even though spaced to have a continuous gap between them, as represented by distance D1 along a path 55, can have the feel of a continuous, soft facing material such that, to the touch, the three-dimensional ink structures and separation gaps are imperceptible from the feel of a continuous non-woven facing material and perform similarly.

In some embodiments, as shown in FIG. 6, an outer-facing surface of a first skin layer 10a of an elastic film 100 can be printed with the three-dimensional ink structures 50, and a core layer 10c can be sandwiched between the first skin layer 10a and a second skin layer 10b. Further, a nonwoven facing can be disposed on an outer-facing surface of the second skin layer 10b.

In some embodiments, the printed two-dimensional ink structures are expanded into three-dimensional ink structures by heating the structures to a temperature greater than about 40° C., or greater than about 60° C. or greater than about 80° C. As further examples, the three-dimensional ink structures can be expanded by heating the structures to a temperature from about 50° C. to about 200° C., such as from about 60° C. to about 180° C., such as from about 80° C. to about 95° C. However, it should be understood that heating or other activation methods desirably should not impact the properties of the underlying film.

Generally, in some embodiments, the three-dimensional ink structures can be expanded by maintaining the structures at the desired temperature for a period of time greater than about 0.5 seconds, such as greater than about 1.0 seconds, such as greater than about 1.5 seconds. In other embodiments, the three-dimensional ink structures can be expanded by maintaining the structures at the desired temperature for a period of time from about 0.5 seconds to about 180 seconds, or from about 1 second to about 90 seconds, or from about 2 seconds to about 60 seconds.

In order to print the three-dimensional ink structures on one or more outer surfaces of the film, the film can first be subjected to a corona treatment, a plasma treatment, or any other treatment that can improve the ink adhesion to the film. For example, corona treatment, which is known in the art of plastic films, generally describes the process of applying an electrical discharge between two narrowly spaced electrodes obtained under atmospheric pressure from a high voltage current. The electrical field generated by the electrodes excites the gas molecules (air) and dissociates some of those molecules to generate a glow of highly energetic species of ions, radicals, metastables and photons. When a polymeric substrate is passed between the two electrodes and is exposed to the glow of active species, changes occur to the polymeric substrate's surface, which usually results in surface oxidation or addition of polar functionalities on the polymeric substrate's surface. These polar functional groups have a strong chemical affinity to the polar chemicals in both the treatment composition as well as in the ink compositions, which results in improved adhesion. Similarly, the more polar polymeric substrate's surface results in an increased surface energy that correlates with improved wettability. For example, the corona treatment may be applied at a level of about 2-50 watts per square foot of web per minute, preferably about 15-40 watts per square foot per minute, more preferably about 8-12 watts per square foot per minute.

Other methods of treating the film may also be employed, for example, a plasma technique under low pressures or atmospheric conditions and under various chemical environments, such as helium, argon, nitrogen, oxygen, carbon dioxide, ammonia, acetylene, and the like, and any mixture or combination thereof. Plasma treatment is mechanistically very similar to corona treatment with the exception that a variety of gases can be injected into the glow discharge to modify the polymeric substrate with a broader range of functional groups. The film can be plasma treated at a level of about 1-25 watts per square foot of web per minute, preferably about 2-20 watts per square foot per minute, more preferably about 3-10 watts per square foot per minute to achieve a surface energy of from about 5 dynes/cm to about 100 dynes/cm, such as from about 10 dynes/cm to about 75 dynes/com, such as from about 15 dynes/cm to about 60 dynes/cm. For instance, in one embodiment, the film can be plasma treated at a 3.2 watt density to achieve a surface energy of about 50 dynes/cm. Further, in some embodiments, such as when the skin layers or outer layer of the film is formed from a polymer material such as a polyester, it is to be understood that corona or plasma treatment may not be necessary.

Regardless of the method used to treat the film, after the film has been treated, the two-dimensional ink structures can be applied or printed on to the film by any suitable method and then activated into three-dimensional ink structures. For instance, the two-dimensional ink structures may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the composition distribution and transfer rate. Gravure printing may provide, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. A suitable example results in about 200 deposits per lineal inch of surface, or about 40,000 deposits per square inch. By providing such a large number of small deposits, the uniformity of the deposit distribution may be enhanced. Suitable gravure printing techniques are also described in U.S. Pat. No. 6,231,719 to Garvey, et al., which is incorporated herein in its entirety by reference thereto for all purposes.

Still another suitable contact printing technique that may be utilized in the present invention is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the fluidic channels are to be printed. The ink is painted onto the screen, and transferred by rubbing the screen (which is in contact with the substrate) with a squeegee.

Ink-jet printing techniques may also be employed in the present invention. Ink-jet printing is a non-contact printing technique that involves forcing the ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

In addition to the printing techniques mentioned above, any other suitable application technique may be used in the present invention. For example, other suitable printing techniques may include laser printing, thermal ribbon printing, piston printing, spray printing, etc. Still other suitable application techniques may include bar, roll, knife, curtain, spray, slot-die, dip-coating, drop-coating, extrusion, stencil application, etc. Such techniques are well known to those skilled in the art.

In one particular embodiment, the printing can be done by a flexographic process with high volume anilox rolls, after which the ink can be dried in-line with warm air. The printed ink can then be activated by heating the substrate to a temperature ranging from about 40° C. to about 250° C., such as from about 60° C. to about 230° C., such as from about 80° C. to about 200° C., or by any other suitable means as discussed above, thereby generating a three-dimensional ink structure that has a "puffed" appearance. It is also to be understood that the aforementioned "puffing" or activating can be done in-line with the printing by combining the drying and puffing steps into the same process.

Though the ink coverage in the form of the three-dimensional ink structures 50 can be adjusted to obtain any desired graphic, in some embodiments, the graphics included continuous discrete small line segments placed adjacent to each other, as well as discrete dots, as shown in FIGS. 5, 7, and 8, to promote tearing in controlled locations. Further, such graphics and spacing as shown help to reduce any restriction to elongation due to the "puffed" three-dimensional ink structures. Alternatively, any of the graphics shown in FIGS. 9 and 10A-10P can be utilized. The interdigitated pattern of FIG. 9 can be utilized to resist tearing or ripping of the film in a continuous line, while the pattern of FIG. 5 can be used to promote intentional tearing or ripping of the film in a continuous line along linear path 55 that is parallel to the three-dimensional ink structures 50, which generally extend in a predominant direction 54.

Further, the extent of activating or puffing of the ink can be controlled by the ink add-on level and thus can be a factor in controlling the hand feel of the material. Generally, the three-dimensional ink structures demonstrate a kinetic coefficient of friction of between about 0.15 and about 0.3, such as from about 0.2 to about 0.25, to provide for a desirable hand, feel, or softness as determined by a slightly modified version of the ASTM D1894-11 standard test method. The friction test plate used was a polished stainless steel #316 with a 1 micro-inch finish. The material to be tested was attached to a coefficient of friction (COF) sled with a weight of 200 grams-force. The sled pin was positioned in the load cell mount of an MTS electromechanical test frame equipped with automated data acquisition capability. The crosshead of the test frame was moved at a constant speed of 10 inches/minute. From the load and displacement data acquired, the kinetic coefficient of friction was calculated as an average of 10 measurements.

Further, in some embodiments, the ink add-on level to the film can range from about 1 wt. % to about 75 wt. %, such as from about 2.5 wt. % to about 65 wt. % such as from about 5 wt. % to about 50 wt. % based on the total weight of the film. Further, the three-dimensional ink structures can cover from about 5% to about 95%, such as from about 10% to about 90%, such as from about 15% to about 85%, such as from about 20% to about 60% of the surface area of an outer surface of the film, such as skin layer 10a. In addition to the graphics, the texture, the appearance, and the feel of the three-dimensional ink structures, as well as the elastic performance of the material, can also be altered by appropriate formulation of the ink. The add-on level and graphics can be suitably designed such that the films or laminates of the present invention have varying hand feel and softness.

III. Facing

While the three-dimensional ink structures described herein can replace the facings on one or both sides of an elastic film, in some embodiments, only one side of the elastic film of the present invention can be adhered or otherwise laminated to a facing, such as a nonwoven facing, to form a laminate. Although any suitable facing can be used, in one embodiment, the facing can be a nonwoven facing that is lightweight and has a low degree of strength in the cross-machine direction ("CD"), which increases the flexibility of the elastic-film/nonwoven facing laminate and also provides significant costs savings in its manufacture. More specifically, the basis weight may range from about 45 grams per square meter or less, in some embodiments from about 1 to about 30 grams per square meter, and in some embodiments, from about 2 to about 20 grams per square meter. Likewise, the nonwoven facing may have a peak load in the cross-machine direction of about 350 grams-force per inch (width) or less, in some embodiments about 300 grams-force per inch or less, in some embodiments from about 50 to about 300 grams-force per inch, in some embodiments from about 60 to about 250 grams-force per inch, and in some embodiments, from about 75 to about 200 grams-force per inch. If desired, the nonwoven facing may also have a low strength in the machine direction ("MD"), such as a peak load in the machine direction of about 3000 grams-force per inch (width) or less, in some embodiments about 2500 grams-force per inch or less, in some embodiments from about 50 to about 2000 grams-force per inch, and in some embodiments, from about 100 to about 1500 grams-force per inch.

The nonwoven facing may be formed from a variety of known processes, and can include a meltblown web, a spunbond web, a bonded carded web, a wetlaid web, an airlaid web, a coform web, etc., as well as combinations of the foregoing. In one particular embodiment, for example, the nonwoven facing is a meltblown facing that contains "microfibers" in that they have an average size of about 15 micrometers or less, in some embodiments from about 0.01 to about 10 micrometers, and in some embodiments, from about 0.1 to about 5 micrometers.

Regardless of the manner in which it is formed, the nonwoven facing can typically be formed from a polymer having a relatively high Vicat softening temperature (ASTM D-1525), such as from about 100° C. to about 300° C., in some embodiments from about 120° C. to about 250° C., and in some embodiments, from about 130° C. to about 200° C. Exemplary high-softening point polymers for use in forming nonwoven facings may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; blends thereof; and so forth. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al., U.S. Pat. No. 4,795,668 to Kruege, et al., U.S. Pat. No. 5,108,820 to Kaneko, et al., U.S. Pat. No. 5,336,552 to Strack et al., U.S. Pat. No. 5,382,400 to Pike, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,057,368 to Largman, et al., U.S. Pat. No. 5,069,970 to Largman, et al., U.S. Pat. No. 5,162,074 to Hills, U.S. Pat. No. 5,277,976 to Hogle et al., and U.S. Pat. No. 5,466,410 to Hills, which are incorporated herein in their entirety by reference thereto for all purposes.

The desired denier of the fibers used to form the nonwoven facing may vary depending on the desired application. Typically, the fibers are formed to have a denier per filament (i.e., the unit of linear density equal to the mass in grams per 9000 meters of fiber) of less than about 6, in some embodiments less than about 3, and in some embodiments, from about 0.5 to about 3.

Although not required, the nonwoven facing may be optionally bonded using any conventional technique, such as by an extrusion casting process, with an adhesive or autogenously (e.g., fusion and/or self-adhesion of the fibers without an applied external adhesive). Suitable autogenous bonding techniques may include ultrasonic bonding, thermal bonding, through-air bonding, calender bonding, and so forth. The temperature and pressure required may vary depending upon many factors including but not limited to, pattern bond area, polymer properties, fiber properties and nonwoven properties. For example, the facing may be passed through a nip formed between two rolls, both of which are typically not patterned i.e., smooth. In this manner, only a small amount of pressure is exerted on the materials to lightly bond them together. Without intending to be limited by theory, such lightly bonded materials can retain a higher degree of extensibility and thereby increase the elasticity and extensibility of the resulting laminate. For example, the nip pressure may range from about 0.1 to about 20 pounds per linear inch, in some embodiments from about 1 to about 15 pounds per linear inch, and in some embodiments, from about 2 to about 10 pounds per linear inch. One or more of the rolls may likewise have a surface temperature of from about 15° C. to about 60° C., in some embodiments from about 20° C. to about 50° C., and in some embodiments, from about 25° C. to about 40° C.

The nonwoven facing may also be stretched in the machine and/or cross-machine directions prior to or after lamination to the elastic film of the present invention. Suitable stretching techniques may include necking, tentering, groove roll stretching, etc. For example, the facing may be necked such as described in U.S. Pat. Nos. 4,981,747, 4,965,122, 5,226,992, and 5,336,545 to Morman, as well as U.S. Patent Application Publication No. 2004/0121687 to Morman, et al. Alternatively, the nonwoven facing may remain relatively inextensible in at least one direction prior to lamination to the film. In such embodiments, the nonwoven facing may be optionally stretched, decoupled, or grooved (incrementally stretched) in one or more directions subsequent to lamination to the film. The facing may also be subjected to other known processing steps, such as aperturing, heat treatments, etc.

If desired, the laminate contemplated by the present invention may also include other facings as is known in the art, such as films, foams, etc. For example, the laminate may include an additional nonwoven facing, such as a meltblown web, spunbond web, bonded carded web, wetlaid web, airlaid web, coform web, etc., as well as combinations of the foregoing. In one particular embodiment, the additional facing may be a bonded carded facing. Fibers of any desired length may be employed in the bonded carded facing, such as staple fibers, continuous fibers, etc. For example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters.

Although not required, the additional facing may also be lightweight and of low strength. For example, the basis weight of the facing may range from about 1 to about 45 grams per square meter (gsm), in some embodiments from about 2 to about 30 gsm, and in some embodiments, from about 3 to about 20 gsm. The facing may also have a peak load in the cross-machine direction ("CD") of about 350 grams-force per inch (width) or less, in some embodiments about 300 grams-force per inch or less, in some embodiments from about 50 to about 300 grams-force per inch, in some embodiments from about 60 to about 250 grams-force per inch, and in some embodiments, from about 75 to about 200 grams-force per inch. If desired, the nonwoven facing may also have a low strength in the machine direction ("MD"), such as a peak load in the machine direction of about 3000 grams-force per inch (width) or less, in some embodiments about 2500 grams-force per inch or less, in some embodiments from about 50 to about 2000 grams-force per inch, and in some embodiments, from about 100 to about 1500 grams-force per inch.

As described above, the additional nonwoven facing may also be stretched in the machine and/or cross-machine directions prior to lamination to the film of the present invention, as well as subjected to other known processing steps, such as aperturing, heat treatments, etc.

IV. Film-Forming and Optional Lamination Technique

The film of the present invention can be formed via any suitable method such as extrusion using a feed block. One method of forming the film by extrusion is discussed below in reference to FIG. 1. Further, if a laminate is formed by adding a facing to one side of the film, where three-dimensional ink structures are present on the other side or the film, in one embodiment, the film can be typically laminated to the facing by directly extruding the film onto a surface of the nonwoven facing as also shown in FIG. 1. If desired, lamination may be facilitated through the use of a variety of techniques, such as adhesives, suctional forces, etc.

Regardless of the lamination technique employed, the selection of an appropriate bonding temperature can help melt and/or soften the thermoplastic polymer(s) of the film so that it may flow and become fused to the nonwoven facing, thereby forming an integral laminate. Furthermore, because the thermoplastic polymer(s) may physically entrap or adhere to the fibers at the bond sites, adequate bond formation may be achieved without requiring substantial softening of the polymer(s) used to form the nonwoven facing. Of course, it should be understood that the temperature of the nonwoven facing may be above its softening point in certain embodiments. To achieve the desired degree of bond formation between the film and nonwoven facing, the temperature at which the elastomeric composition is extruded is typically from about 50° C. to about 300° C., in some embodiments from about 60° C. to about 275° C., and in some embodiments, from about 70° C. to about 260° C.

Various embodiments of the film-forming and optional lamination technique of the present invention will now be described in greater detail. FIG. 1 illustrates a process for forming a multilayer film and a laminate containing the multilayer film and a facing. Referring to FIG. 1, film 10 is formed from a film coextrusion apparatus 40 such as a cast or blown unit which could be in-line or off-line. Typically the apparatus 40 will include two or three extruders 41. To make the core layer, filled resin including the polymer matrix material is prepared in a mixer (not shown) and directed to an extruder 41. To make each skin layer, the polymer components are extruded on one or both sides of the core layer. The multilayer film 10 can then be cooled on a chill roller 42. A vacuum box 43 can help maintain the film close to the surface of the chill roller. Air knives or electrostatic pinners 44 also urge the film 10 against the roller surface.

From the film extrusion apparatus 40 or off-line rolls supplied, the multilayer film 10 can be optionally directed to a film stretching unit 47 having a plurality of stretching rollers 46a-e, which progressively stretch and thin the film in the machine direction, which is the direction of travel of the film. The rollers 46a-e can be heated and apply an amount of stress and progressively stretch the multilayer film 10 to a stretched length. The number of rollers may be greater or less depending on the level of stretch desired and the amount of stretching between each pair of rollers. The optimum stretch temperature varies with the core layer and skin layer polymers used in the film 10, and is generally below the melting temperature of the matrix polymer in the core layer.

Further, although not required, the multilayer film 10 may be laminated to one or more substrates, such as a nonwoven facing, using conventional adhesive bonding or thermal bonding techniques known in the art. The type of substrate and bonding will vary depending on the particular end use application. Referring again to FIG. 1, film 10 may be laminated to nonwoven facing 30 immediately after the film is stretched. In one embodiment, a nonwoven facing 30, which can be a spunbond web or a meltblown web, is unwound from a supply roll 62. The nonwoven facing material 30 then passes through the nip 64 of S-roll arrangement 66, formed by a stack of rollers 68 and 70. The nonwoven facing material 30 can then be passed under spray equipment 72 which sprays adhesive 73 through die head 74 onto a surface of the nonwoven facing 30. With or without the adhesive treatment, the nonwoven facing 30 can then be joined to multilayer film 10 and bonded between calender rollers 58, which can be heated if necessary. The resulting laminate 32 can be wound and stored on a supply roll 60. Further, in some embodiments, the laminate 32 can be grooved prior to being wound and stored on the supply roll 60 to enhance stretchability as discussed below in more detail.

When the elastic film of the present disclosure is adhered to a facing such as a nonwoven web as discussed in detail above, it is to be understood that the two-dimensional ink can be printed on the outer surface of the film that is not adhered to the nonwoven facing either before or after adhering the film to the nonwoven facing. The specific processes that can be used to print the two-dimensional ink onto the film are discussed in more detail above.

It is to be understood that various additional potential processing and/or finishing steps known in the art, such as slitting, stretching, etc., may be performed to activate the laminate to render it elastically active without departing from the spirit and scope of the invention. In one embodiment, the nonwoven facing and/or a skin layer can be decoupled to render the original material elastic. Alternatively, the laminate may optionally be mechanically stretched in the cross-machine and/or machine directions to enhance extensibility and activate the elastic components of the laminate. For example, the laminate may be coursed through two or more rolls that have grooves in the CD and/or MD directions that incrementally stretch the laminate in the CD and/or MD direction depending on the desired direction of stretch. For instance, if the three-dimensional ink structures 50 are printed in a generally continuous linear path 54 along the machine direction as in FIG. 5, the grooves in the nonwoven facing can be formed in the machine direction as well, where the grooves can be formed in the gap 55 between separate continuous path(s) 54 of the three-dimensional ink structures 50. Such grooving will then provide stretch that is generally perpendicular to the machine direction, such that the laminate is stretchable in the cross-machine direction. On the other hand, if the three-dimensional ink structures are generally continuous in a linear path along the cross-machine direction as in FIG. 11, the grooves in the nonwoven facing can be formed in the cross-machine direction as well, where the grooves can be formed in the gap 55 between separate generally linear continuous path(s) 54 of the three-dimensional ink structures. Such grooving will then provide stretch that is generally perpendicular to the cross-machine direction, such that the laminate is stretchable in the machine direction. Meanwhile, in other embodiments, grooving of the nonwoven facing can be carried out in both the cross-machine direction and machine direction of the laminate to promote biaxial stretching of the laminate in both the cross-machine direction and machine direction, such as in FIG. 8 or 10E, 10F, 10G, 10H, 10I, 10J, 10K, or 10L. Further, it should also be understood that in some embodiments, grooving of the nonwoven facing and film can eliminate the need for the continuous gap (e.g., reference numerals 55, 56, and 57 in FIGS. 2B, 3, 4, 5, 7, 8, and 11) between the three-dimensional printed structures 50 because the grooving can promote stretching even in the absence of a continuous gap, although the gap can further enhance the stretchability of the film and may be desired in other embodiments.

Such grooved satellite/anvil roll arrangements are described in U.S. Patent Application Publication Nos. 2004/0110442 to Rhim, et al. and 2006/0151914 to Gerndt, et al., which are incorporated herein in their entirety by reference thereto for all purposes. The grooved rolls may be constructed of steel or other hard material (such as a hard rubber). In one embodiment, the multilayered film can be activated by grooving at a depth where the elongation of the material achieved is beyond the yield elongation of the elastic core layer and the thermoplastic skin layers. The grooving described above can break the facing component of the laminate in such a way to permit the laminate to stretch and recover elastically.

If desired, heat may be applied to the laminate just prior to or during the application of incremental stretch to cause it to relax somewhat and ease extension. Heat may be applied by any suitable method known in the art, such as heated air, infrared heaters, heated nipped rolls, or partial wrapping of the laminate around one or more heated rolls or steam canisters, etc. Heat may also be applied to the grooved rolls themselves. It should also be understood that other grooved roll arrangement are equally suitable, such as two grooved rolls positioned immediately adjacent to one another.

Besides the above-described grooved rolls, other techniques may also be used to mechanically stretch or activate the laminate in one or more directions. For example, the laminate may be passed through a tenter frame that stretches the laminate. Such tenter frames are well known in the art and described, for instance, in U.S. Patent Application Publication No. 2004/0121687 to Morman, et al. The laminate may also be necked. Suitable techniques necking techniques are described in U.S. Pat. Nos. 4,981,747, 4,965,122, 5,226,992, and 5,336,545 to Morman, as well as U.S. Patent Application Publication No. 2004/0121687 to Morman, et al., all of which are incorporated herein in their entirety by reference thereto for all purposes. Another approach for activating the laminate involves decoupling of the facing and or the thermoplastic skin layer(s) from the elastic core layer to render the core layer elastic.

It is to be understood that the various laminate activation methods discussed above (decoupling, grooving, stretching, etc.) can take place either before or after application of the ink. Surprisingly, the present inventors have discovered that the grooving activation methods described above do not damage the two dimensional ink structures, which means that the ink can be printed onto the film before the film is attached to the nonwoven facing, which also means that the two-dimensional ink structures can be activated into three-dimensional ink structures by heat or any other method and the film can be activated by grooving simultaneously and in a more efficient manner.

Moreover, in some embodiments, the film component of the laminate can be ultrasonically bonded as a means to promote intentional tearing or ripping of the film at desired locations on demand, such as at the gap between adjacent three-dimensional ink structures.

V. Articles

The film or laminate of the present invention may be used in a wide variety of applications. The resulting film or laminate may be used in a wide variety of personal care absorbent articles and medical articles. An "absorbent article" generally refers to any article capable of absorbing water or other fluids. Typically, absorbent articles include a substantially liquid-impermeable layer (e.g., outer cover), a liquid-permeable layer (e.g., bodyside liner, surge layer, etc.), and an absorbent core disposed between the liquid-impermeable layer and the liquid-permeable layer. Absorbent articles include without limitation diapers, training pants, swim wear, absorbent underpants, adult incontinence products, feminine hygiene products, and the like. Medical products include medical garments, underpads, bandages, drapes, medical wipes, and the like. Examples of other absorbent articles include, swim wear, baby wipes, and so forth, food service wipers, clothing articles, and so forth. Materials and processes suitable for forming such absorbent articles are well known to those skilled in the art.

In one particular embodiment, the film or laminate of the present invention can be a component of an absorbent personal care article that includes an elastic side panel. The film or laminate can be a component of the elastic side panel, and the three-dimensional ink structures on an outer surface of the film can form a pattern that is a series of lines. In such an embodiment, the spacing between the lines can be used as an unfastening region for the absorbent personal care article. Further, the three-dimensional ink structures can provide the elastic side panel with the desired hand or feel, much in the same manner as would a nonwoven facing that covered the entire elastic film component of the side panel, but in a more cost efficient manner by only covering a portion of the elastic film component. In another embodiment, the film or laminate of the present invention may be used in elastic waist, leg cuff/gasketing, stretchable ear, stretchable outer cover, and chassis applications.

The present invention may be better understood with reference to the following examples.

Test Methods

Tensile Properties

Tensile measurements were conducted on a Sintech 1S electro-mechanical test frame equipped with MTS Test Works data acquisition capabilities. The cross-head speed used was 20 inches/minute. Rectangular specimens having dimensions of 3 inches by 7 inches were loaded in the jaws of the fame at a gauge length of 3 inches. The load-displacement data was collected at specified time intervals. From knowledge of the load and displacement, the elongation at break and corresponding load at break were obtained. The toughness of the material was calculated by integrating the area under the load-displacement curve.

In the case of the notched specimen examples, samples were notched using a new razor blade that was used one time per sample. A 0.5 millimeter notch was introduced in the unprinted portions of the laminate material as well as the portions of the laminate material printed with the three-dimensional structures. All tensile test conditions were the same as described above except a gauge length of 2 inches was used to collect the data.

EXAMPLE 1

The ability to form a laminate including a multilayered film with three-dimensional ink structures printed on one side and a nonwoven facing on the other side was demonstrated. A three layer film was made on a film line equipped with single screw extruders fitted with a feed block and a film die such that a three layer film could be made. The three layer film includes a 90 wt. % core layer positioned between two 5 wt. % skin layers. The core layer was 99 wt. % VISTAMAXX™ 6102 plastomer and 1 wt. % titanium dioxide pigment, while each of the skin layers was 65 wt. % DOWLEX™ 2107 linear low density polyethylene (LLDPE), 34 wt. % DOWLEX™ 2517 LLDPE, and 1 wt. % titanium dioxide pigment. For Samples 1-3 described below, the film was extrusion cast onto a chill roll, which was then fed into the nip of two calendar rolls, where a 15 gsm polyethylene spunbond facing was adhesively attached, under pressure, to one side of the three layer film. Next, the resulting laminate was plasma treated at a density of 3 watts per square foot per minute to achieve a surface energy greater than 45 dynes/centimeter on the film side of the laminate. The outer-facing surface of the film (i.e., the surface not adjacent the spunbond facing) was then printed with AQUAPUFF™ blue ink with a flexographic printing system using an anilox roll having a volume of 30 billions of cubic microns (bcm) in the pattern shown in FIG. 2A. The ink was printed in a generally linear continuous path along the machine direction such that a gap was present between each of the generally linear continuous paths. The ink was dried in-line with forced air draft through a heated oven by keeping the substrate at 38° C. Then, the substrate was heated to 110° C. for 1 minute to puff the ink from a two-dimensional structure to a three-dimensional structure.

Meanwhile, for Sample 4, a three layer film including the same components as described above in reference to Samples 1-3 was extrusion cast onto a chill roll, which was then fed into the nip of two calendar rolls, where a 15 gsm polyethylene spunbond facing was adhesively attached, under pressure, to each side of the three layer film.

Next, mechanical testing was performed on Samples 1-4. Sample 1 was a laminate including a film printed on one side with three-dimensional ink structures and adhered to a 15 gsm polyethylene nonwoven facing on the other side that was tested as is without any notches formed in the sample. Sample 2 was a laminate formed as in Sample 1 where a 5 mm notch was formed in a section of the film side of the laminate containing a three-dimensional puffed ink structure. Sample 3 was a laminate formed as in Sample 1 where a 5 mm notch was formed in a section of the film side of the laminate containing only film and no three-dimensional puffed ink structure. Sample 4 was a laminate including the film formed as described above which was positioned between two 15 gsm polyethylene nonwoven facings (without any three-dimensional ink structure present). The results from the tensile testing are shown below in Table 1.

TABLE 1

| Sample | Elongation at Break (%) | Load at Break (gram-force) | Toughness (lb · in) |
|---|---|---|---|
| 1 | 400 | 2600 | 50 |
| 2 | 130 | 1100 | 2 |
| 3 | 80 | 920 | 1 |
| 4 | 770 | 3100 | 84 |

As shown in Table 1, the laminate that included an elastic film having three-dimensional ink structures printed on one side and a spunbond facing on the other side (Sample 1) exhibited a lower load at break and elongation % at break compared to the laminate that included an elastic film disposed between two spunbond facings (Sample 4), although Sample 1 still exhibits acceptable properties for an elastic laminate.

As also shown in Table 1, laminates containing a film that includes three-dimensional ink structures on one outer surface are more likely to break, rip or tear first at the gap in the film where no three-dimensional ink structures are present, as evidenced by a comparison of samples 2 and 3. For instance, when a notch was formed in a three-dimensional ink structure on the film (Sample 2), the film could elongate to 130% before breaking, while when a notch was formed in a gap on the film containing no ink structure (Sample 3), the film could only elongate to 80% before breaking. Thus, by controlling the location of printed three-dimensional ink structures on an outer surface of a film, the location of intentional (on demand) tearing or ripping of the film can be controlled.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An elastic film having a machine direction and a cross-machine direction, the film comprising a first outer-facing surface, a second outer-facing surface, and three-dimensional ink structures, wherein each of the three-dimensional ink structures is present on the first outer-facing surface in a pattern extending in a predominant direction, wherein the three-dimensional ink structures cover from about 15% to about 85% of a surface area of the first outer-facing surface, wherein a continuous gap exists between adjacent three-dimensional ink structures, wherein the film is stretchable along the continuous gap in a direction that is generally perpendicular to the predominant direction in which the three-dimensional ink structures extend, and wherein the three-dimensional ink structures comprise a heat-activatable expandable ink, wherein the three-dimensional ink structures have been formed as a result of heat treatment of the heat-activatable expandable ink at a temperature ranging from about 95° C. to about 200° C. for a time period ranging from about 60 seconds to about 180 seconds, wherein the three-dimensional ink structures exhibit an expansion in height of at least 0.025 millimeters of a height of the heat-activatable expandable ink prior to expansion and have a height ranging from about 0.05 millimeters to about 5 millimeters, wherein the heat-activatable expandable ink includes thermoplastic microspheres and an elastomeric polymer present in an amount in a range from greater than 0 wt. % to about 10 wt. % based on the total weight of the three-dimensional ink structures, wherein the pattern of three-dimensional ink structures is configured to promote tearing of the film in a direction parallel to the predominant direction in which the three-dimensional ink structures extend, wherein the film comprises a core layer, a first skin layer, and a second skin layer, wherein the core layer is positioned between the first skin layer and the second skin layer, wherein the core layer comprises a propylene-based plastomer or ethylene-based plastomer.

2. The film of claim 1, wherein the pattern comprises an individual line, groups of lines, groups of S-shapes, groups of discrete dots, groups of repeating geometric shapes, or combinations thereof.

3. The film of claim 1, wherein the predominant direction of the pattern runs along the machine direction of the film, and further wherein the continuous gap runs along the machine direction of the film.

4. The film of claim 1, wherein the predominant direction of the pattern runs along the cross-machine direction of the film, further wherein the continuous gap runs along the cross-machine direction of the film.

5. The film of claim 1, wherein the three-dimensional ink structures have a width in either the machine direction or cross-machine direction ranging from about 0.25 mm to about 25 mm, wherein the width is perpendicular to the predominant direction of the pattern.

6. The film of claim 1, wherein the continuous gap spans a distance in either the machine direction or the cross-machine direction ranging from about 0.5 mm to about 20 mm, wherein the distance is perpendicular to the predominant direction of the pattern.

7. An absorbent personal care article comprising the film of claim 1.

8. A laminate comprising the film of claim 1 and a nonwoven facing layer, wherein the nonwoven facing layer is attached to the second, outer-facing surface.

9. The film of claim 1, wherein the first skin layer and the second skin layer comprise a linear low density polyethylene.

10. The film of claim 1, wherein the predominant direction of the pattern is at an angle that ranges from about 15° to about 90° relative to the cross-machine direction of the film.

11. A film having a machine direction and a cross-machine direction, the film comprising a first outer-facing surface, a second outer-facing surface, and three-dimensional ink structures, wherein each of the three-dimensional ink structures is present on the first outer-facing surface in a pattern extending in a predominant direction, wherein the three-dimensional ink structures cover from about 15% to about 85% of a surface area of the first outer-facing surface, wherein a continuous gap exists between adjacent three-dimensional ink structures, wherein the film is elastic or inelastic, and wherein the three-dimensional ink structures comprise a heat-activatable expandable ink, wherein the three-dimensional ink structures have been formed as a result of heat treatment of the heat-activatable expandable ink at a temperature ranging from about 95° C. to about 200° C. for a time period ranging from about 60 seconds to about 180 seconds, wherein the three-dimensional ink structures exhibit an expansion in height of at least about 0.025 millimeters of a height of the heat-activatable expandable ink prior to expansion and have a height ranging from about 0.05 millimeters to about 5 millimeters, wherein the heat-activatable expandable ink includes thermoplastic microspheres and an elastomeric polymer present in an amount in a range from greater than 0 wt. % to about 10 wt. % based on the weight of the three-dimensional ink structures, wherein the pattern of three-dimensional ink structures is configured to promote tearing of the film in a direction parallel to the predominant direction in which the three-dimensional ink structures extend the film comprises a core layer, a first skin layer, and a second skin layer, wherein the core layer is positioned between the first skin layer and the second skin layer, wherein the core, wherein layer comprises a propylene-based plastomer or ethylene-based plastomer.

12. The film of claim 1, wherein the core layer has a thickness ranging from about 20 to about 200 micrometers.

* * * * *